United States Patent
Hassett et al.

(10) Patent No.: US 10,704,076 B2
(45) Date of Patent: Jul. 7, 2020

(54) MULTI-TIERED HIGH THROUGH-PUT SCREEN FOR COMPOUNDS EFFECTIVE AGAINST BACTERIAL BIOFILM AND COMPOUNDS EFFECTIVE FOR INHIBITING AND ERADICATING BACTERIAL BIOFILM

(71) Applicants: University of Cincinnati, Cincinnati, OH (US); Government of the United States as Represented by the Secretary of the Air Force, Wright-Patterson AFB, OH (US)

(72) Inventors: Daniel J. Hassett, Cincinnati, OH (US); Thomas J. Lamkin, Cincinnati, OH (US); Warunya Panmanee, Cincinnati, OH (US); Deborah E. Taylor, Cincinnati, OH (US); Chloe J. A. Shea, Cincinnati, OH (US)

(73) Assignees: University of Cincinnati, Cincinnati, OH (US); Government of the United States as Represented by the Secretary of the Air Force, Wright-Patterson AFB, OH (US)

( * ) Notice: Subject to any disclaimer, the term of this patent is extended or adjusted under 35 U.S.C. 154(b) by 0 days.

(21) Appl. No.: 16/224,006

(22) Filed: Dec. 18, 2018

(65) Prior Publication Data
US 2019/0127776 A1    May 2, 2019

Related U.S. Application Data

(62) Division of application No. 14/776,043, filed as application No. PCT/US2014/028149 on Mar. 14, 2014, now Pat. No. 10,202,631.
(Continued)

(51) Int. Cl.
*C12Q 1/18* (2006.01)
*A61K 31/175* (2006.01)
(Continued)

(52) U.S. Cl.
CPC .............. *C12Q 1/18* (2013.01); *A01N 37/10* (2013.01); *A01N 37/28* (2013.01); *A01N 41/06* (2013.01); *A01N 43/12* (2013.01); *A01N 43/38* (2013.01); *A01N 43/42* (2013.01); *A01N 43/44* (2013.01); *A01N 43/52* (2013.01); *A01N 43/54* (2013.01); *A01N 43/56* (2013.01); *A01N 43/80* (2013.01); *A01N 43/82* (2013.01); *A01N 43/90* (2013.01); *A01N 47/38* (2013.01); *A61K 31/175* (2013.01); *A61K 31/18* (2013.01); *A61K 31/216* (2013.01); *A61K 31/343* (2013.01); *A61K 31/404* (2013.01); *A61K 31/4155* (2013.01); *A61K 31/4184* (2013.01); *A61K 31/425* (2013.01); *A61K 31/4245* (2013.01); *A61K 31/435* (2013.01); *A61K 31/4545* (2013.01); *A61K 31/4709* (2013.01); *A61K 31/496* (2013.01); *A61K 31/506* (2013.01); *A61K 31/519* (2013.01); *C07C 69/738* (2013.01); *C07C 243/28* (2013.01); *C07C 311/21* (2013.01); *C07D 209/08* (2013.01); *C07D 215/52* (2013.01); *C07D 215/56* (2013.01); *C07D 231/20* (2013.01); *C07D 235/18* (2013.01); *C07D 271/12* (2013.01); *C07D 275/03* (2013.01); *C07D 307/92* (2013.01); *C07D 401/04* (2013.01); *C07D 405/04* (2013.01); *C07D 405/14* (2013.01);
(Continued)

(58) Field of Classification Search
CPC ....................................................... C12Q 1/18
USPC ................................................................ 506/9
See application file for complete search history.

(56) References Cited

U.S. PATENT DOCUMENTS 5,811,471 A * 9/1998 Shanbrom ............... A61F 13/36
                                                521/141
6,329,165 B1  12/2001 Chattoraj et al.
(Continued)

OTHER PUBLICATIONS

International Preliminary Report on Patentability for corresponding PCT Application No. PCT/US2014-028149 dated Sep. 24, 2015.
(Continued)

*Primary Examiner* — Karla A Dines
(74) *Attorney, Agent, or Firm* — Dinsmore & Shohl LLP

(57) ABSTRACT

A high through-put screening method for identifying agents effective for inhibiting biofilm formation and/or killing established biofilm are disclosed. The method includes three tiers, and each tier includes three specific biological process assays. The tier levels are a primary screen, a confirmation screen, and a dose-response screen, and the biological process assays include assays for total bacterial growth, bacterial metabolic activity, and biofilm formation. The series of assays may be run once or more than once at each tier. A library of compounds is subject to tier A and only compounds meeting a primary parameter advance to tier B, and only tier B compounds meeting a confirmation parameter advance to tier C, and only tier C compounds meeting a dose-response parameter are identified as putative agents effective for inhibiting and/or eradicating a biofilm, further wherein the assays are conducted for each compound subject to the respective tier. The method is effective and validated for identifying agents which inhibit and/or kill *Staphylococcus epidermidis, Pseudomonas aeruginosa,* and *Acinetobacter baumannii* biofilms. Agents identified according to the high through-put screen and validated in follow-up experiments as effective for inhibiting and/or killing bacterial biofilms are also disclosed.

13 Claims, 11 Drawing Sheets

Related U.S. Application Data

(60) Provisional application No. 61/781,474, filed on Mar. 14, 2013.

(51) Int. Cl.

| | | |
|---|---|---|
| A61K 31/18 | (2006.01) | |
| A61K 31/343 | (2006.01) | |
| A61K 31/404 | (2006.01) | |
| A61K 31/4155 | (2006.01) | |
| A61K 31/4184 | (2006.01) | |
| A61K 31/4245 | (2006.01) | |
| A61K 31/425 | (2006.01) | |
| A61K 31/435 | (2006.01) | |
| A61K 31/4545 | (2006.01) | |
| A61K 31/4709 | (2006.01) | |
| A61K 31/496 | (2006.01) | |
| A61K 31/506 | (2006.01) | |
| A61K 31/519 | (2006.01) | |
| A01N 37/10 | (2006.01) | |
| A01N 37/28 | (2006.01) | |
| A01N 41/06 | (2006.01) | |
| A01N 43/12 | (2006.01) | |
| A61K 31/216 | (2006.01) | |
| A01N 43/38 | (2006.01) | |
| A01N 43/42 | (2006.01) | |
| A01N 43/44 | (2006.01) | |
| A01N 43/52 | (2006.01) | |
| A01N 43/54 | (2006.01) | |
| A01N 43/56 | (2006.01) | |
| A01N 43/80 | (2006.01) | |
| A01N 43/82 | (2006.01) | |
| A01N 43/90 | (2006.01) | |
| A01N 47/38 | (2006.01) | |
| C07C 69/738 | (2006.01) | |
| C07C 243/28 | (2006.01) | |
| C07C 311/21 | (2006.01) | |
| C07D 209/08 | (2006.01) | |
| C07D 215/52 | (2006.01) | |
| C07D 215/56 | (2006.01) | |
| C07D 231/20 | (2006.01) | |
| C07D 235/18 | (2006.01) | |
| C07D 271/12 | (2006.01) | |
| C07D 275/03 | (2006.01) | |
| C07D 307/92 | (2006.01) | |
| C07D 401/04 | (2006.01) | |
| C07D 405/04 | (2006.01) | |
| C07D 405/14 | (2006.01) | |
| C07D 413/04 | (2006.01) | |
| C07D 471/04 | (2006.01) | |
| C07D 491/052 | (2006.01) | |

(52) U.S. Cl.
CPC ......... *C07D 413/04* (2013.01); *C07D 471/04* (2013.01); *C07D 491/052* (2013.01)

(56) References Cited

U.S. PATENT DOCUMENTS

| | | |
|---|---|---|
| 2008/0166753 A1 | 7/2008 | Storey et al. |
| 2011/0189260 A1 | 8/2011 | Herr et al. |
| 2014/0155844 A1* | 6/2014 | Isch .............. A61M 25/00 604/307 |

OTHER PUBLICATIONS

Lauren M. Junker et al, "High-Throughput Screens for Small-Molecule Inhibitors of Pseudomonas aeruginosa Biofilm Development"; Antimicro. Agents Chemother. 2007, 51 (10: 3582-3590); Published Jul. 30, 2007.

Julie A. Wu et al, "Lysostaphin Disrupts *Staphylococcus aureus* and *Staphylococcus epidermidis* Biofilms on Artificial Surfaces"; Antimicrob. Agents Chemother. 2003, 47 (11): 3407-3414. Jul. 2003.

Chloe J. A. Shea, Effectiveness of Novel Compounds at Inhibiting and Killing P. aeruginosa and S. epidermidis Biofilms; Thesis submitted to the Graduate School of the University of Cincinnati, Feb. 20, 2012.

Elvers et al., Journal of Industrial Microbiology and Biotechnology, 2002, 29, pp. 331-338 (Year: 2002).

\* cited by examiner

MULTI-TIERED HIGH THROUGH-PUT SCREEN FOR COMPOUNDS EFFECTIVE AGAINST BACTERIAL BIOFILM AND COMPOUNDS EFFECTIVE FOR INHIBITING AND ERADICATING BACTERIAL BIOFILM

RELATED APPLICATIONS

This application is a divisional of U.S. application Ser. No. 14/776,043, filed Sep. 14, 2015, which is a § 371 National Stage Entry of PCT/US14/28149, filed Mar. 14, 2014, which claims the benefit of U.S. Provisional Application No. 61/781,474, filed Mar. 14, 2013, the entire disclosures of which are incorporated herein by this reference.

TECHNICAL FIELD

The present invention relates generally to methods for identifying compounds effective for the inhibition of bacterial biofilm formation and killing of established bacterial biofilms, and to compounds and compositions of compounds identified as effective. More particularly, the invention relates to a high through-put screening method for identification of compounds effective for inhibiting *Staphylococcus epidermidis, Pseudomonas aeruginosa* and *Acinetobacter baumannii* biofilm formation, and for identification of compounds effective at killing established *Staphylococcus epidermidis, Pseudomonas aeruginosa* and *Acinetobacter baumannii* biofilms, and to compounds and compositions of compounds so-identified.

BACKGROUND

Bacteria have employed several mechanisms to survive in the diverse environments they encounter. One such mechanism is the ability to form a biofilm, a bacterial community consisting of both viable and dead bacteria enmeshed in a complex of protein, nucleic acids, lipids and carbohydrates. Biofilm formation begins with the attachment of bacteria to a surface, the production of extracellular polymeric substances by the bacteria, and maturation of biofilm as other microbes and materials are added to the matrix. Microorganisms are known to be capable of adhering to any surface, including stainless steel, teflon, the widely used plastic polyvinyl chloride (PVC), and even the high grade plastic material polyvinylidene fluoride (PVDF). As such, bacteria can form biofilms on any number of substrates in industrial, marine, military, and residential settings including water and sewage pipes, food processing equipment, cooling or heating water systems, fuel systems, off shore oil and gas pipelines, boat hulls, toilets, drains, and sinks. In many cases biofilms formed on these surfaces causes corrosion of materials which require costly repair and are a hazard to environmental and personal safety. Further, biofilms can pose an infectious threat when bacteria disperse from the biofilm into food and water supplies. Biofilm-forming bacteria are also a serious threat in medical environments where they are commonly found on tubing, catheters, stents, prostheses and heart valves. Moreover, bacterial biofilms can also found on bone, teeth, and other tissues and by one estimate, are responsible for 80% of all infections of the human body that include middle ear infections, gingivitis, endocarditis, and urinary tract infections.

The ability of bacteria to form a biofilm enables microorganisms to adhere, persist, and even thrive on countless materials in diverse environments. The biofilm matrix protects embedded bacteria from changes in pH, temperature, nutrient and oxygen content. The biofilm matrix also induces dramatic changes in bacterial gene regulation, metabolism, and resistance that facilitate bacterial growth and survival in adverse conditions. Biofilm bacteria are also extremely resistant to biocides used in medical, industrial, residential and military settings to decontaminate equipment, infrastructure, and devices as well as to treat infected patients. Investigators have reported that biofilm bacteria were 150 to more than 3000 times more resistant to hypochlorous acid (free chlorine, pH 7.0) than planktonic bacteria. The food industry reported similar findings, which necessitate the use of high concentrations of chlorine to rid processing facilities of contaminating biofilm-forming microbes and the need to find better disinfectants. Not surprisingly, the biofilm matrix also impedes host-mediated response to infection, and confers resistance to an array of antibiotics typically used to treat bacterial infections.

Three of the most problematic opportunistic bacteria associated with highly refractory infections in hospitals and clinics around the world are *Pseudomonas aeruginosa, Acinetobacter baumannii*, and *Staphylococcus epidermidis*. *P. aeruginosa*, a Gram-negative bacterium, ranks fourth as the most common nosocomial pathogen accounting for approximately ten percent of all hospital-acquired infections (41). *A. baumannii*, a Gram-negative bacterium, found in intensive care type settings where immune-compromised patients are intubated, have multiple intravenous lines or monitoring devices, surgical drains, or indwelling urinary catheters. *A. baumannii* has been particularly problematic in infections of wounded U.S. military personnel over the past decade during the Iraq and Afghanistan war, and has also been reported in water pipes. *S. epidermidis* is a common Gram-positive organism that comprises the majority of the human commensal skin microflora, and depending on the strain and the immune status of the patient, can also cause severe hospital-acquired infections, primarily associated with indwelling medical devices. Staphylococcal species have been identified as contaminates in drinking water, on food processing equipment and other environmental surfaces.

Biofilms of the "Mode I" variety are commonly known as surfaced-attached microbial communities that are sculpted strategically by microbes embedded within them as highly complex structures composed of well-developed matrices of live and dead organisms, as well as polysaccharides, nucleic acids, lipids and proteins. Mode II biofilms are not surface-attached and comprised of organisms such as *P. aeruginosa* that are attached to one another in macrocolonies enmeshed in thick, highly inspissated mucus in airway diseases such as cystic fibrosis (CF) and chronic obstructive pulmonary disease (COPD) *Pseudomonas* biofilms can also be found growing on medical devices, in water and sewage pipes, in swimming pools fuels, and fuel systems.

As the cells within a biofilm differentiate and a biofilm matures, reduced metabolic rates, the cellular expression of defense mechanisms and the reduced ability of antimicrobial agents to penetrate the biofilm result in increased antimicrobial resistance and make a biofilm particularly difficult to eradicate. Present biofilm control strategies typically target the early stages of biofilm development and involve the use of toxic antimicrobial agents. However such toxic agents present their own downstream problems due to their release into the environment.

A chemical library is a collection of stored chemicals typically generated, for example, from specific synthetic or functional goals, or from a series of untargeted synthetic efforts, and/or from purchases and acquisitions of smaller libraries. Each chemical in a library has associated information stored in some kind of database, such as the chemical structure, purity, quantity, and physiochemical characteristics of the compound. Many thousands of well-categorized chemical libraries are known to exist and such libraries have found particular use in high through-put screening in the drug development industry.

The development of high-through put screening platforms for identifying agents effective against biofilms, however, poses particular challenges. The matrix-encased biofilm is specialized for surface persistence and biofilms may be highly resistant to antibiotics effective against planktonic bacteria of the same species. The matrix itself may provide a barrier to penetration by a biocide. The individual bacterial cells are typically metabolically less active than their dispersed counterparts, and therefore may be less susceptible to effects of an anti-microbial agent. Cells in a biofilm are also thought to develop a protected biofilm phenotype, for example by up-regulation and increased expression of drug efflux pumps. Hence, modalities which are effective against planktonic bacteria, and which are most amenable to testing and filtering via high through-put assay platforms, may have substantially reduced efficacy or be completely ineffective against the same bacteria residing in a biofilm.

Inhibition of biofilm formation may be effectively achieved by interfering with or preventing adhesion; however an inhibiting agent may be completely ineffective against an established biofilm and may in fact exhibit very little antibiotic activity. An antibiotic agent may be very effective at inhibiting biofilm formation simply by controlling the bacterial population, but may have little or no impact on an established biofilm. Further, an agent may exhibit efficacy with respect to killing an established biofilms by mechanisms relating to interference with colonization or association of bacterial cells, such as by triggering dispersal rendering dispersed bacteria vulnerable to antibiotics effective against planktonic cells, and yet the same agent may not exhibit any antibiotic activity itself.

Further, bacterial biofilms are often comprised of more than one species of bacteria. Agents capable of inhibiting biofilm formation of more than one species known to co-reside in biofilms are particularly desirable, and yet non-toxic agents capable of killing established biofilm colonies formed from multiple bacterial species are virtually unknown.

There remains a need for safe, non-toxic agents having efficacy in inhibiting biofilm formation and/or killing established bacterial biofilm. Clearly it would be advantageous to develop high-through methods for screening libraries of compounds to identify novel agents effective for inhibiting bacterial biofilm formation and/or killing established bacterial biofilm.

SUMMARY

Accordingly, the present investigators developed a novel multi-tiered high through-put screening assay for identifying agents effective in inhibiting bacterial biofilm formation and for killing established biofilms. A large small-molecule compound library was subject to the high-through put screen (HTS) of the instant invention and novel single, dual, and broad spectrum agents capable of inhibiting bacterial biofilm formation and/or killing bacteria resident in one or more of *P. aeruginosa*, *A. baumannii* and *S. epidermidis* biofilms were identified. The HTS hits were confirmed and validated using confocal laser scanning microscopy (CLSM). A minimum inhibitory concentration (MIC) was determined and toxicity investigations were conducted for each broad spectrum agent identified.

One embodiment of the instant invention provides a high through-put screening method (HTS) for identifying agents from a library of compounds for efficacy in inhibiting bacterial biofilm formation and killing established biofilm. The method comprises conducting three tiers of three assays, each assay selected to reflect a different mechanism of effect. It is understood that "tiers" are levels of screening that filter compounds such that fewer compounds are run in subsequent tiers. Three tiers according to some embodiments of the invention comprise (A) a primary screen, (B) a confirmation screen, and (C) a dose-response screen. The confirmation tier repeats the assays run in the primary screen at the same concentration of compound; however in multiple trials, and compounds advance to the next tier only if a rule-in parameter is reached in all of the multiple trials. This increases reliability of a positive result providing a more robust statistical model of a "hit." A dose-response screen comprises running the assays multiple times at different concentrations and generating dose-response curves for each compound in each assay.

The assays included in the HTS are selected to reflect a variety of possible mechanistic underpinnings to a desired effect. The assays according to one specific embodiment include a total bacterial growth assay, a bacterial metabolic activity assay, and a biofilm formation assay. The library of compounds is subject to tier A and only compounds meeting a primary rule-in parameter advance to tier B. Only tier B compounds meeting a rule-in confirmation parameter advance to tier C, and only tier C compounds meeting a rule-in dose-response parameter are ultimately identified as putative agents effective for inhibiting formation of a bacterial biofilm and/or for killing an established biofilm. The series of assays are conducted for each compound subject to the respective tier. The putative agents may be termed HTS "hits" which are then subject to confirmation/validation by Confocal Laser Scanning Microscopy (CLSM) assay. CLSM hits may be termed "confirmed hits" and may be subject to follow-up testing, for example, toxicity testing.

According to other embodiments of the invention, compounds and compositions effective for inhibiting formation of a bacterial biofilm, and/or effective for killing an established bacterial biofilm, wherein the bacteria is one (single), two (dual) or three (broad spectrum) of *S. epidermidis*, *P aeruginosa* and *A. baumannii*, are also provided. Table 1 sets forth novel single, dual and broad spectrum agents in accordance with embodiments of the invention.

These and other embodiments and aspects of the instant invention will be further understood and clarified by reference to the Detailed Description, Figures and Examples set forth below.

Figure 2:
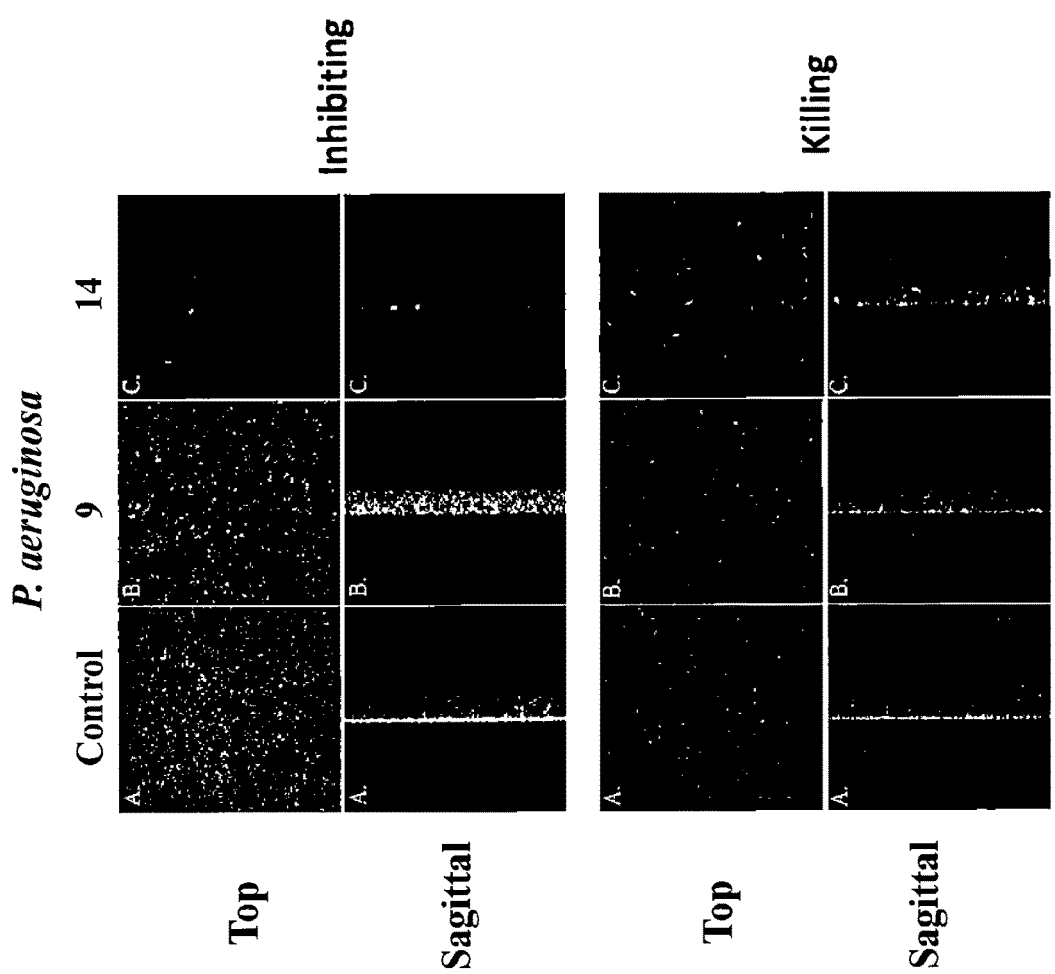

FIG. 2: This figure shows Confocal Laser Scanning Microscopic images of compounds effective for inhibiting *P. aeruginosa* biofilm formation and/or killing *P. aeruginosa* biofilm.

Figure 3A:
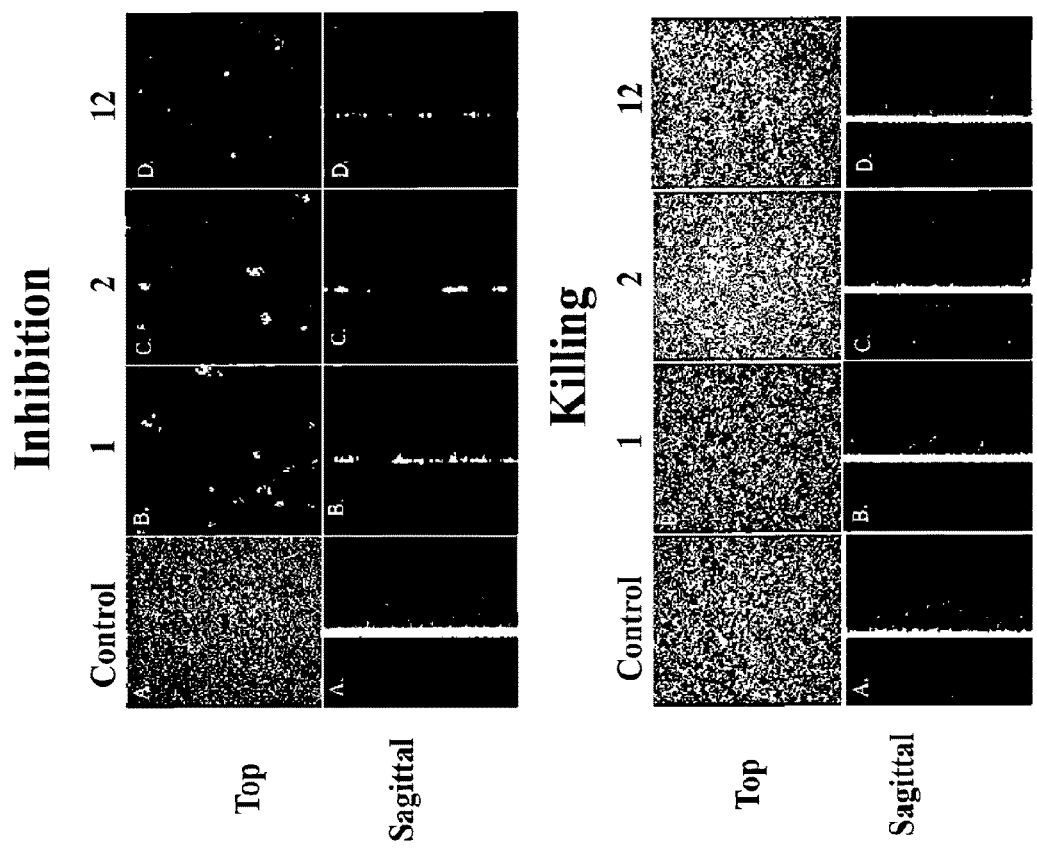

FIG. 3A: This figure shows Confocal Laser Scanning Microscopic images of compounds effective for inhibiting formation of and/or killing *A. baumannii* (Ab) biofilm; 3B: this figure shows Confocal Laser Scanning Microscopic images of compounds effective for inhibiting formation of and/or killing *P. aeruginosa* (Pa) biofilm.

Figure 4:
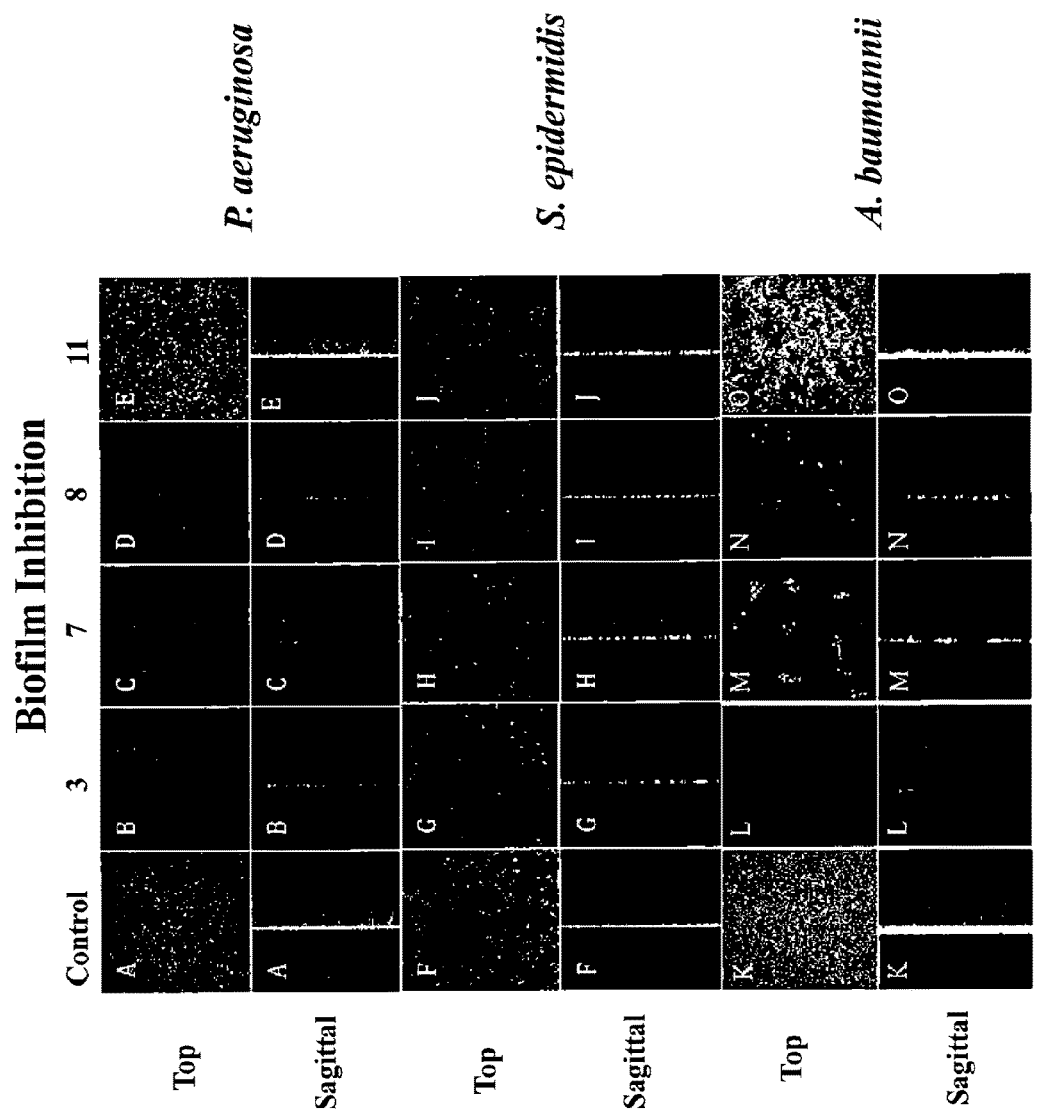

FIG. 4: This figure shows Confocal Laser Scanning Microscopic images of compounds effective for inhibiting *P. aeruginosa* (Pa) or *S. epidermidis* (Sa) or *A. baumannii* (Ab) biofilm formation.

Figure 5:
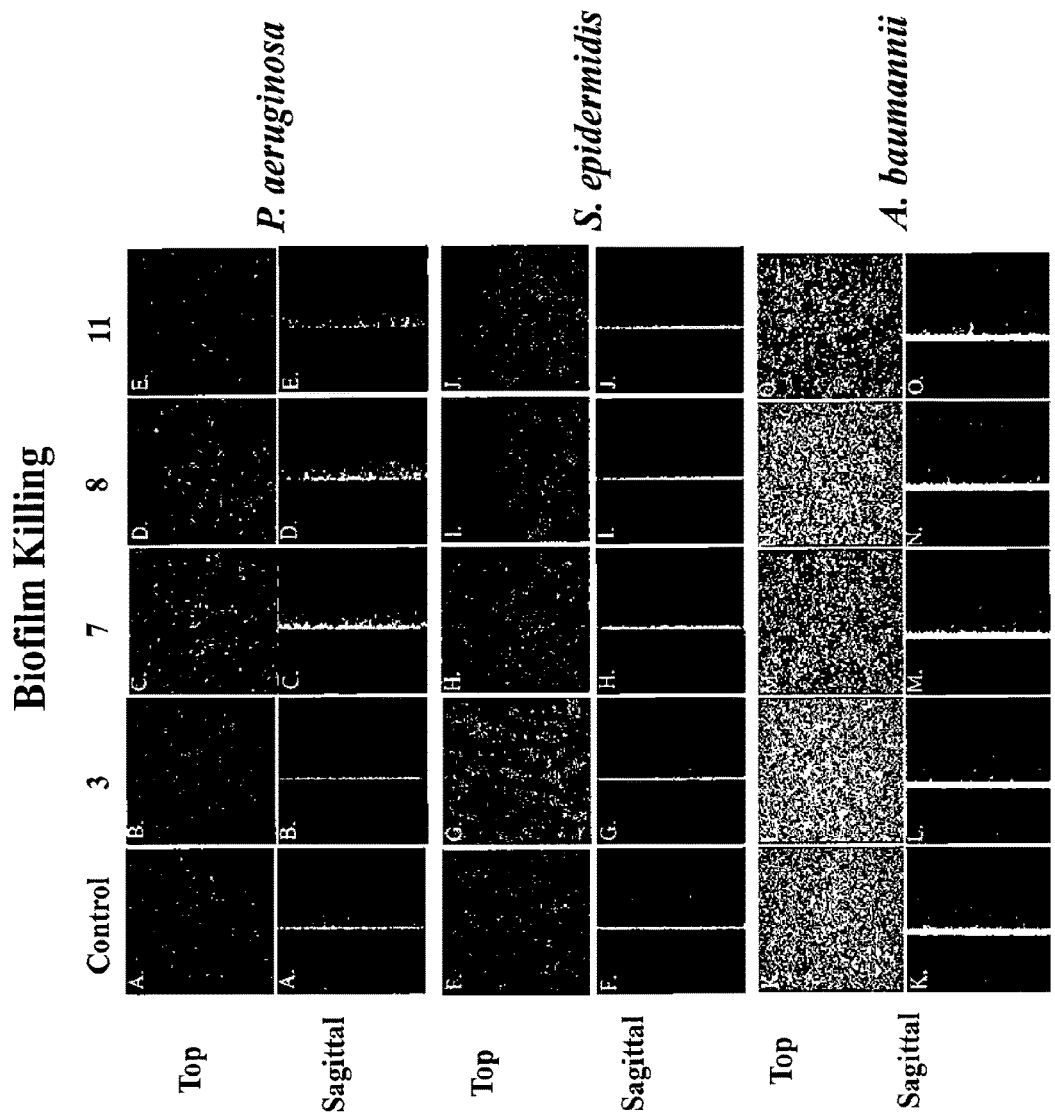

FIG. 5: This figure shows Confocal Laser Scanning Microscopy results for compounds effective for killing an established *P. aeruginosa* (Pa) or *S. epidermidis* (Se) or *A. baumannii* (Ab) biofilm.

Figure 6A:
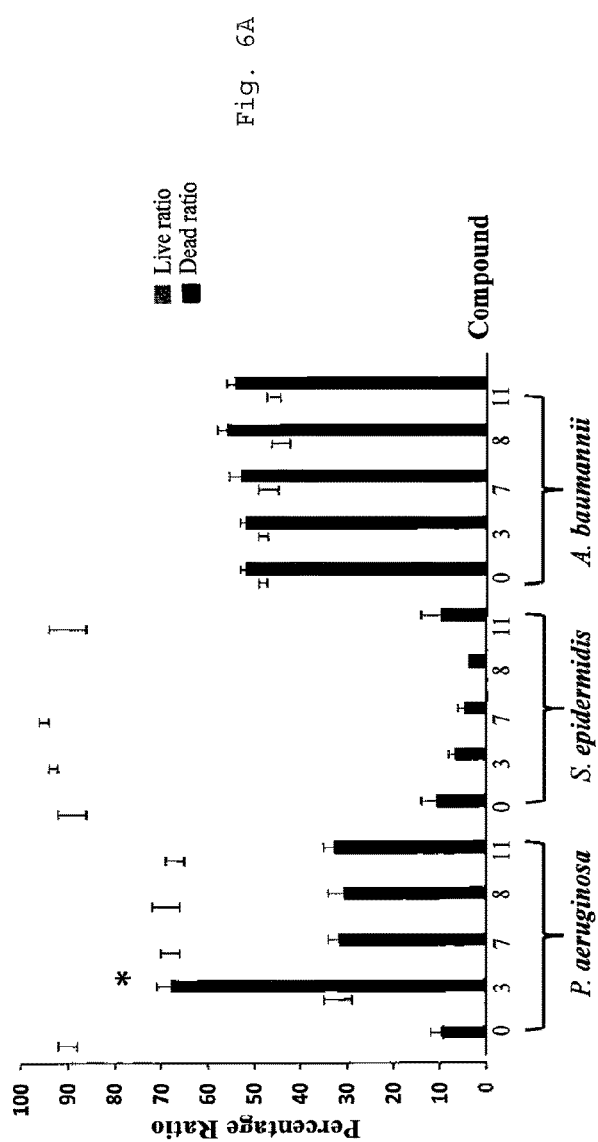

FIG. 6A: Illustrates the ratio of live to dead cells after treatment with one of compounds 3, 7, 8 or 11 on *P. aeruginosa* (Pa), *S. epidermidis* (Se) and *A. baumannii* (Ab) biofilm; (6B) shows the ratio of live to dead cells after treatment with one of compounds 18, 24, 26, and 31 on *A. baumannii* (Ab) biofilm.

Figure 7:
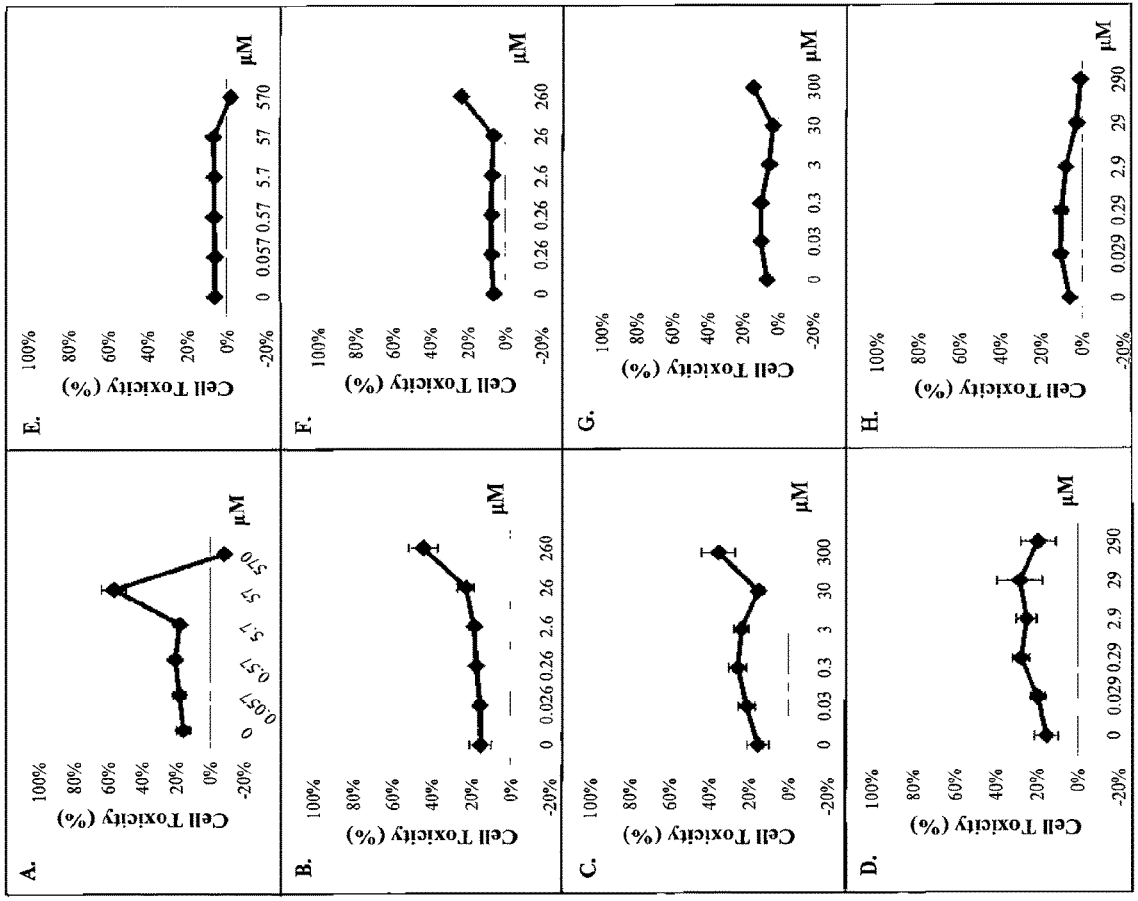

FIG. 7: Illustrates cytotoxicity of broad spectrum compounds on differentiated THP-1 and A549 cell lines. The cytotoxicity of each compound was determined by an LDH activity assay. Various concentrations of compounds were used to treat the cells, and cytotoxicity was calculated compared to controls.

Figure 8:
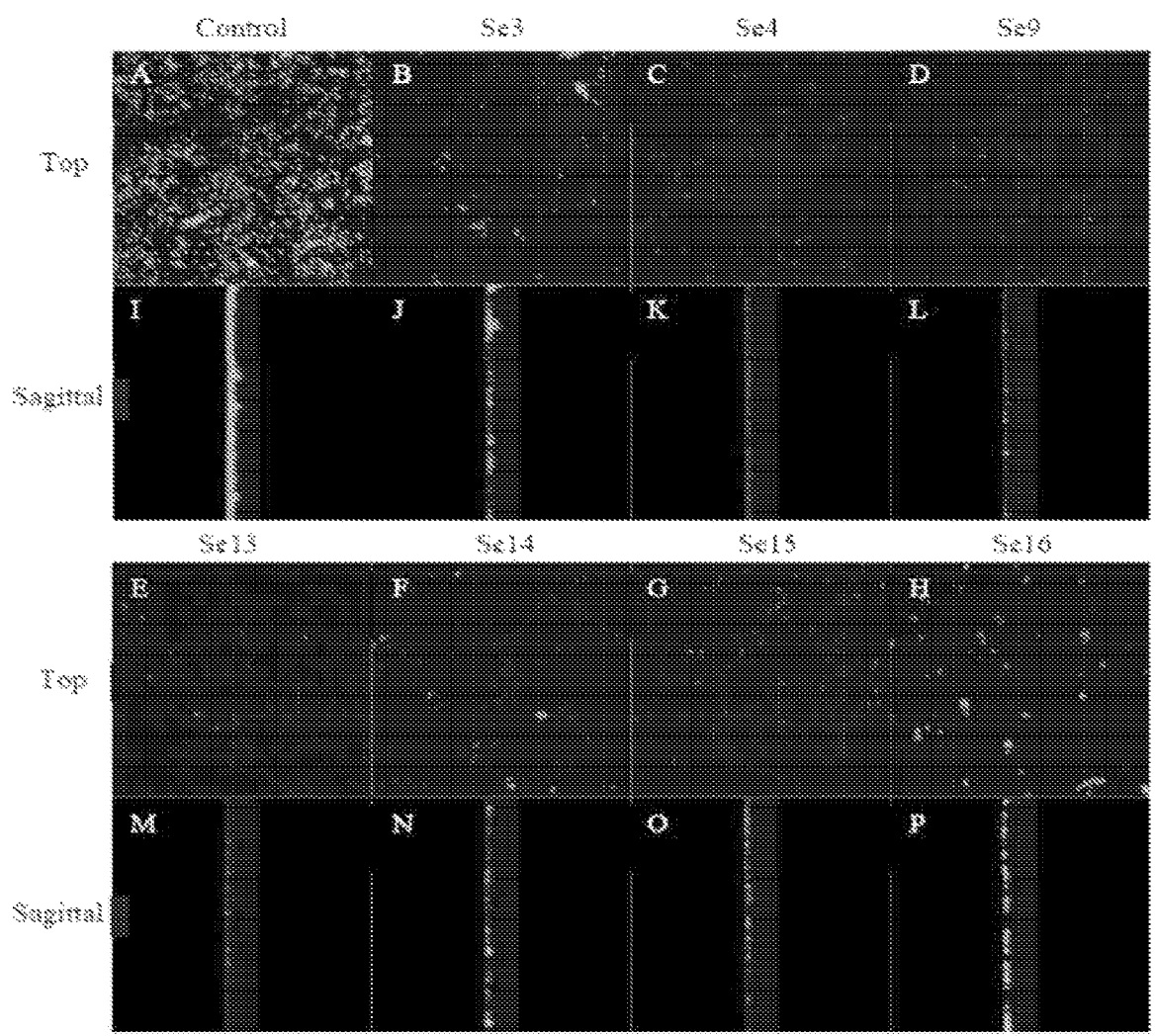

FIG. 8: shows compounds effective at inhibiting *S. epidermidis* (Se) biofilm formation.

Figure 9:
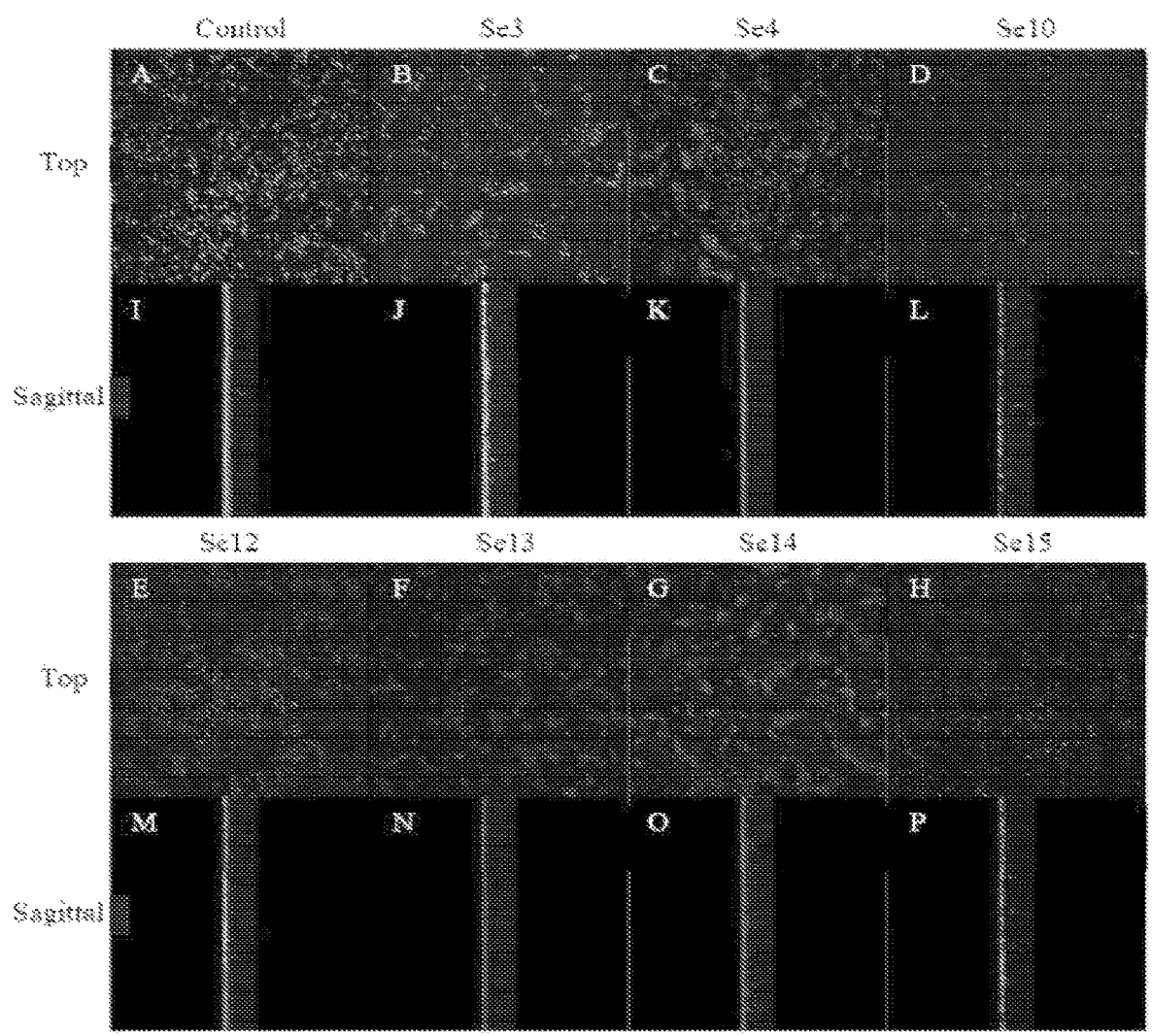

FIG. 9: shows compounds effective at killing established *S. epidermidis* (Se) biofilm.

DETAILED DESCRIPTION

*Pseudomonas aeruginosa* (Pa), *Staphylococcus epidermidis* (Se), and *Acinetobacter baumannii* (Ab) are opportunistic human bacterial pathogens. They are particularly dangerous due to their ubiquitous nature and capacity to form antibiotic-resisting biofilm infections, and are a growing source of healthcare-associated infections.

Pa is a Gram-negative, rod-shaped bacterium that can grow under both aerobic and anaerobic conditions. It is one of the most common opportunistic pathogens that affect humans. Infection is especially prevalent and dangerous in cystic fibrosis patients, where it inhabits the airways, but is also a danger for cancer patients, burn victims, and individuals with compromised immune systems.

Se is a Gram-positive coccus capable of surviving in both aerobic and anaerobic conditions by switching from respiration to fermentation. It is a normal component of human flora, and usually survives on the skin without harming its host. However, Se biofilms can grow on catheters and other medical implants inserted into the body, and are a major source of biomaterial infections. Se is another important opportunistic pathogen that can cause serious illness in immune-compromised patients.

Ab is a Gram-negative rod and is strictly aerobic. It frequently emerges in outbreaks, particularly in intensive care units, and drug resistance is becoming a large problem worldwide, especially in shrapnel related accidents in the wars in Iraq and Afghanistan. The sources of infection are similar to that of Pa and Ab; those persons undergoing invasive surgery, people with catheters, and people exposed to high amounts of antibiotics are at the highest risk for infection.

Taken together, Pa, Se, and Ab are three extremely prevalent microorganisms whose pervasive presence and a decreasing supply of effective medicine make them important targets for new treatments. Although a variety of antimicrobials exist for combating Pa, Se, and Ab infections, and common disinfectants are used for eliminating microorganisms from surfaces to which biofilms may attach, all three of these microorganisms are becoming increasingly resistant to both antibiotics and disinfectants. Pa has a wide variety of mechanisms through which resistance is developed or possessed innately; it can prevent the access to the antibiotic through multidrug efflux pumps; inactivate the antibiotics through β-lactamases; and rapidly acquire mutations in vivo allows it to develop new defenses. Ab can also express β-lactamases that offer resistance, and multidrug efflux pumps have been found present in resistant strains. Moreover, Ab can rapidly transfer antimicrobial-resistance genes from resistant to susceptible strains. Se has also developed mechanisms of resistance to certain antibiotic treatments. For example, it can escape neutrophil digestion and can detect antimicrobial peptides. Finally, the biofilm structures themselves confer resistance, as their organized arrangement prevents antibiotics from accessing the majority of bacteria. The antimicrobials to which these biofilms are resistant include kanamycin for Pa, methicillin and vancomycin for Se, and ciprofloxacin for Ab; resistance is so extensive that some strains express some form of resistance to almost every available antibiotic, and the implanted device must be surgically removed to eliminate the biofilm.

Embodiments of the present invention provide a novel and effective high through-put screen (HTS) for identifying agents from a compound library capable of inhibiting bacterial biofilm formation or killing an established biofilm. "Killing an established biofilm" in accordance with the instant disclosure means one or more of disrupting adhesion of the biofilm, killing resident bacteria, and triggering dispersal of the biofilm. The high through-put screening method has three screening tiers, and each tier comprises running at least one series of three distinct biological process assays. The three tiers include (A) a primary screen, (B) a confirmation screen, and (C) a dose-response screen. In specific embodiments, the assays comprise (a) a total bacterial growth assay, (b) a bacterial metabolic activity assay, and (c) a biofilm formation assay. A library of compounds is screened according to tier A and only compounds meeting a rule-in primary parameter advance to tier B. Only tier B compounds which meet a rule-in confirmation parameter advance to tier C. The tier C compounds which meet a rule-in dose-response parameter are identified as putative agents effective for inhibiting biofilm formation and/or killing an established biofilm.

According to specific embodiments, a total bacterial growth assay may comprise an optical density measurement, a bacterial metabolic activity assay may comprise a resazurin indicator, and a biofilm formation assay may comprise crystal violet staining; each assay being conducted in the presence of a specific concentration of a compound subject to a tier.

In a very specific embodiment, a rule-in parameter for a compound to move from tier A to tier B is one of ≥80% inhibition in (a), ≥80% inhibition in (b), and ≥60% inhibition in (c). A rule-in confirmation parameter required for a compound to move from tier B to tier C is based on three trials with ≥60% inhibition in (a), (b) or (c) across all three trials. Requirement for a rule-in triplicate increases the statistical robustness of a "hit." A rule-in dose-response parameter, for example, is a calculated $AC_{50} \leq 20$ μM in at least one of (a), (b) or (c). Generally, the concentration of a compound used for purposes of tier (A) is the same concentration used in tier (B). The dose-response screen typically comprises generating multiple dose-response curves for inhibition in each of (a), (b), and (c), the dose response curves comprise a number of concentration-response data points sufficient to provide statistical significance to a parameter. In an exemplary embodiment, for example, three dose-response curves are generated for inhibition in each of (a), (b), and (c), and the dose-response curves comprise data points at 10 different concentrations for each compound subject to the tier. A person or ordinary skill in the art, however, will understand how to determine the number of data points required to achieve a desired level of statistical significance in a given empirical protocol.

Once HTS hits are identified, the effects of the HTS hit compounds on inhibition of biofilm formation and killing existing biofilms is confirmed and validated. In a specific embodiment, confirmation and validation are by Confocal Laser Scanning Microscopy (CLSM).

According to specific embodiments of CLSM confirmation of efficacy in killing established biofilms, a biofilm is permitted to grow and establish, and CLSM is performed on the established biofilm. "Mode I" biofilms include surface-attached microbial communities formed as a matrix of live and dead organisms, as well as polysaccharides, nucleic acids, lipids and proteins. "Mode II" biofilms are not surface-attached and the bacterial cells attach to one another in macrocolonies and may exist as masses of associated bacterial cells suspended in liquid media. The inventive HTS is effective for identifying agents which inhibit and kill either or both of a Mode I and Mode II biofilm. For example, *Staphylococcus epidermidis* forms a Mode I biofilm and *Pseudomonas aeruginosa* and *Acinetobacter baumannii* typically form Mode II biofilms.

Other embodiments of the invention are directed to compounds identified as effective for inhibiting biofilm formation and/or killing established biofilm. The compounds according to the invention are identified through the HTS methods and subject to follow-up confirmation whereupon they are referred to herein as "confirmed hits." Additional investigation may include, for example, toxicity testing. Compounds identified as effective for inhibiting bacterial biofilm formation or for killing established bacterial biofilm, wherein the bacteria is one or more of *S. epidermidis, P aeruginosa* and *A. baumannii*, are set forth in Table 1. Single agents include those effective against one bacterial species. Dual agents include those effective against two bacterial species, and broad spectrum agents are effective against either or both of inhibition and killing in all three bacterial species.

Compositions effective for inhibiting bacterial biofilm formation and/or for killing established biofilms comprising one or more of the compounds set forth in Table 1 are also contemplated. Articles of manufacture, including, for example, medical devices and instrumentation, hospital and other treatment facility surfaces, nursery appliances and toy surfaces, fabrics and wound dressing materials intended to contact human skin vulnerable to bacterial infection may comprise one or more of the identified compounds.

The HTS hit compounds are divided into 3 groups based on their effectiveness on a specific microorganism, such as single agent compounds effective on *A. baumannii* (compounds 17, 18, 21, 23, 24, 25, 26, 29, 30, 31 and 33) or *P. aeruginosa* (compounds 9 and 14), or dual agent compounds comprising those that were effective on both bacterial species (compounds 1, 2 and 12). Another group of compounds is characterized as broad spectrum agents based on efficacy for inhibiting *A. baumannii* and *P. aeruginosa*, and *S. epidermidis* biofilm formation and/or killing established biofilms of these species (compounds 3, 7, 8 and 11).

CLSM was used to investigate all of the HTS hit compounds in two ways. First, the effectiveness of each compound for inhibiting formation of a biofilm was assessed. Then, the effectiveness of each compound in killing established biofilms was assessed. The results are summarized in Table 4.

Compounds 1, 2, 3, 7, 12, 17, 18 and 29 possessed the same effect at inhibiting biofilm formation in both HTS assay and CLSM experiments. Among this group, compound 12 failed to kill *P. aeruginosa* biofilms when examined by CLSM. The compounds from the HTS hit list that failed to duplicate the results of biofilm inhibition in CLSM assay include compounds 11 (for *A. baumannii* and *P. aeruginosa*), 9, 21, 23-26 and 30-33. Interestingly, compound 14 showed the opposite effect. With the exception of compound 31, this latter group of compounds also failed to kill bacteria within a biofilm as summarized in Table 3. Compound 8 was more effective at inhibiting *A. baumannii* and *P. aeruginosa* biofilm formation by CLSM (10 μM) than would have been predicted based on the higher $AC_{50}$ observed in the HTS assay for biofilm formation, 31.56 μM and 44.39 μM, respectively.

Figure 1A:
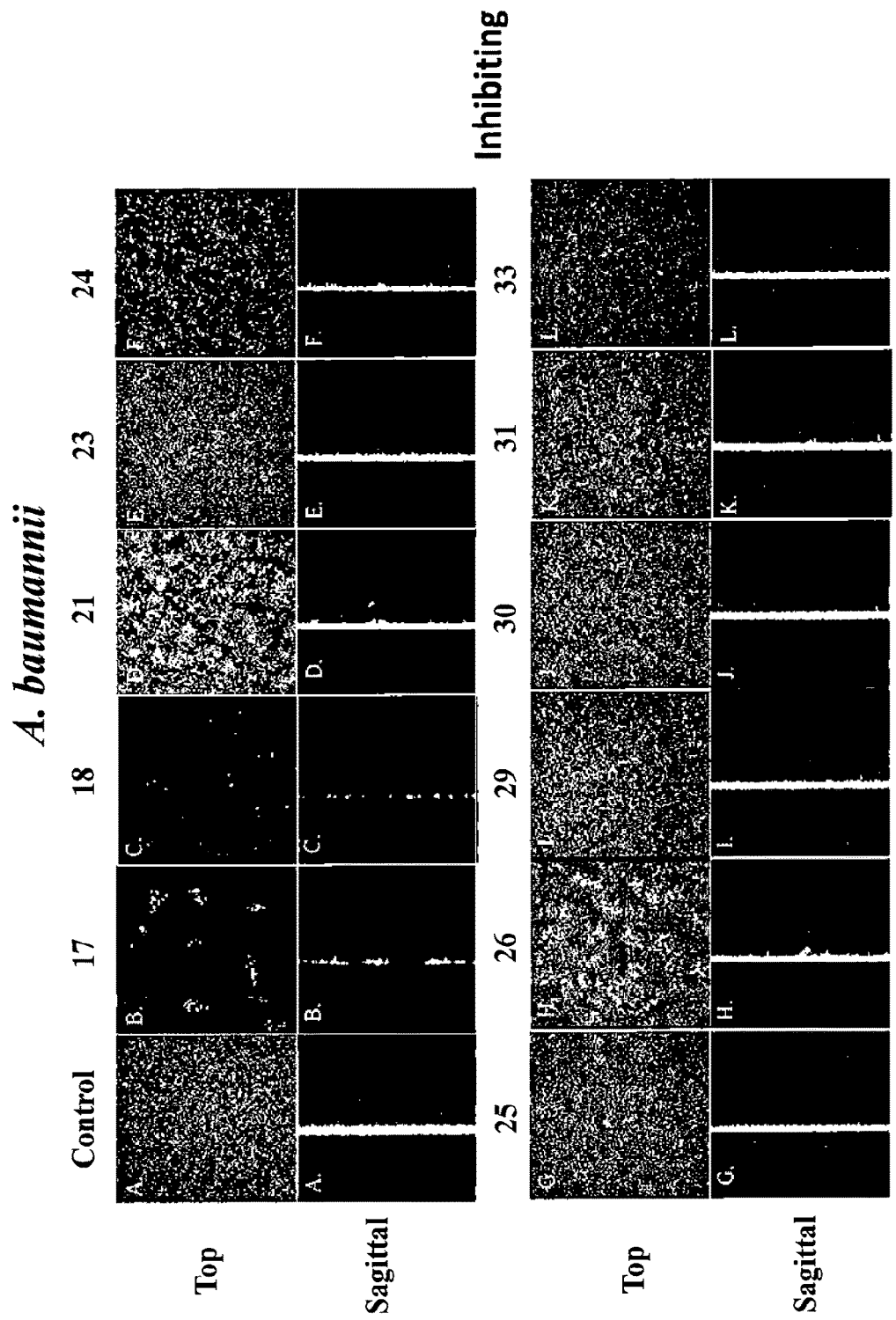
FIG. 1A: Confocal Laser Scanning Microscopic images showing the effect of compounds from HTS assay which inhibit *A. baumannii* (Ab) biofilm formation; efficacy for inhibition of biofilm formation was assessed by growing biofilms on a confocal friendly chamber in the presence of 10 µM compound for 18 hours. 1B: Confocal Laser Scanning Microscopic images showing the effect of compounds from HTS assay which kill *A. baumannii* (Ab) biofilm; efficacy for killing resident bacteria of an established biofilm was assessed by growing biofilm without compound present for 18 hours then treating with 300 µM compound for 24 hours. Biofilm cells were then stained with viability stain and a ratio of live vs. dead bacteria was assessed by confocal laser scanning microscopy.
Figure 1B:
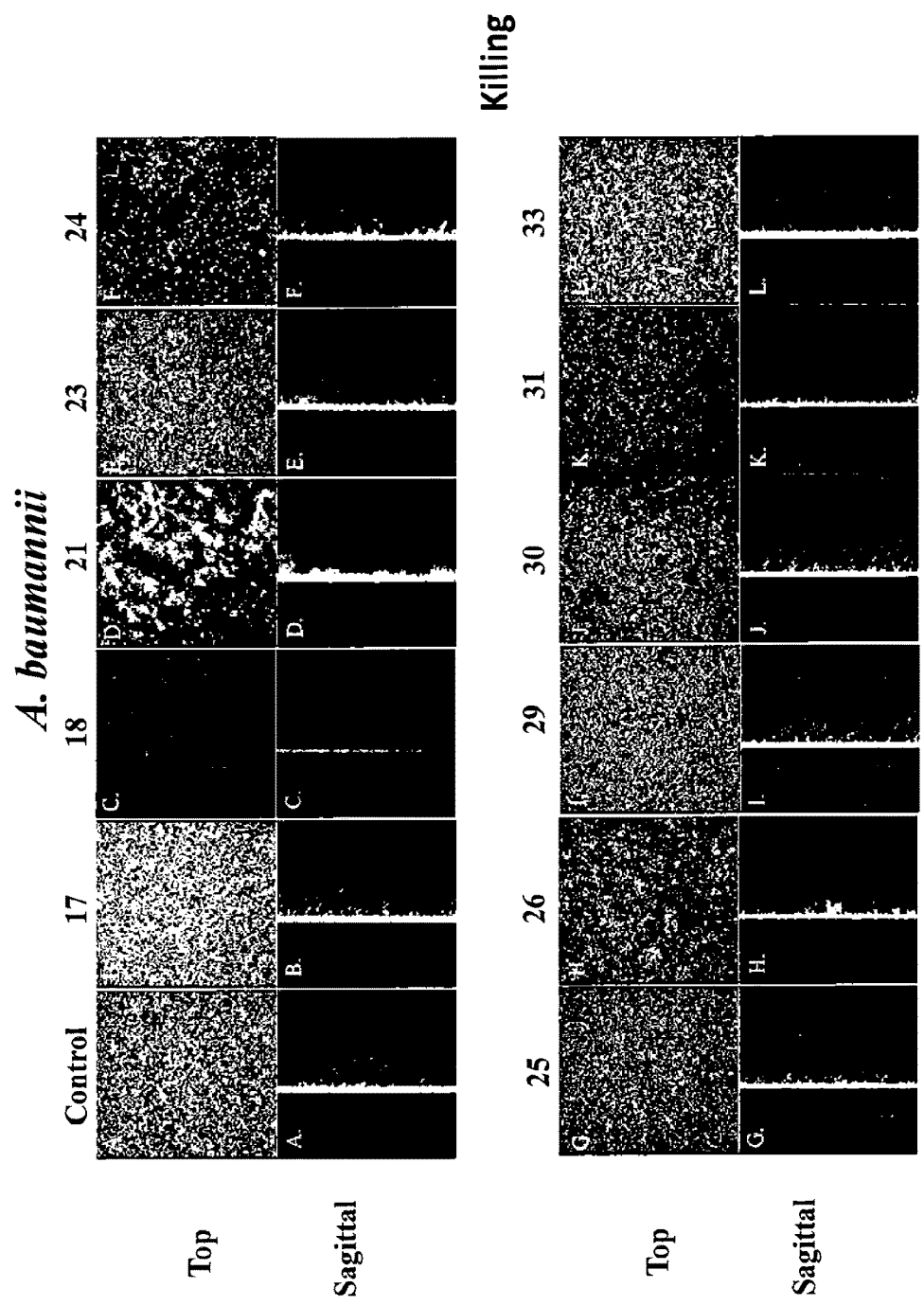
Figure 3B:
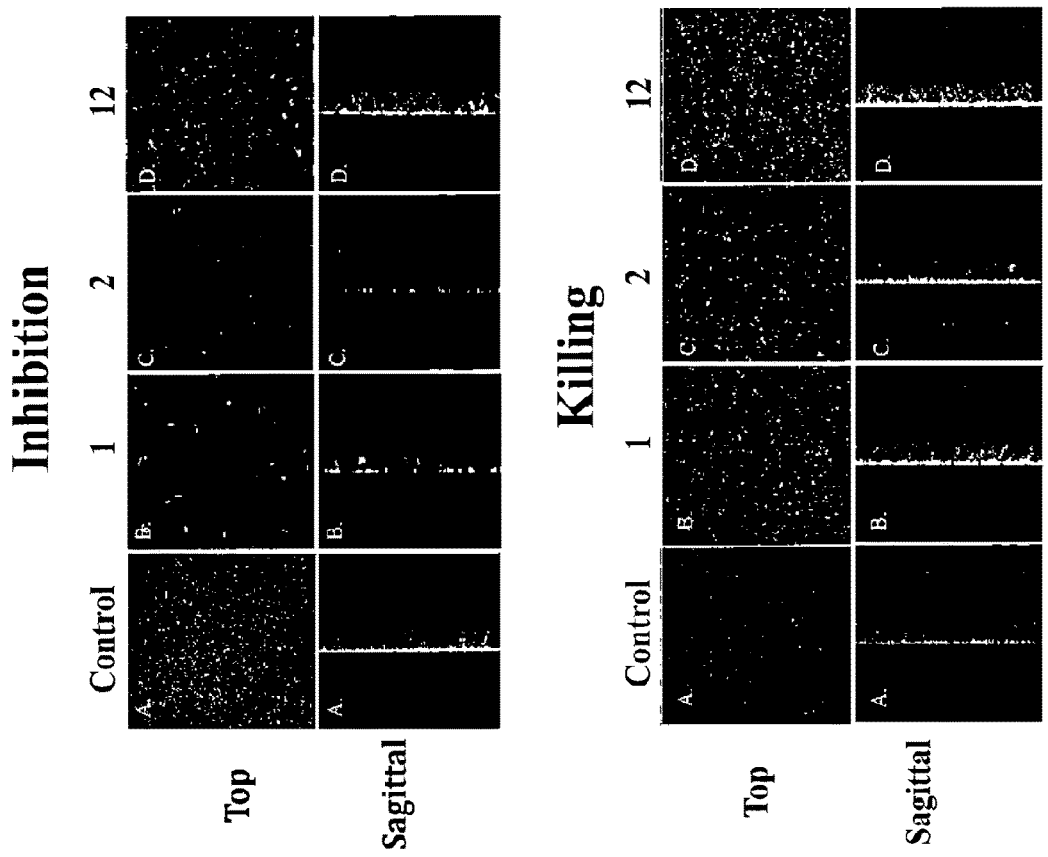

The CLSM results also indicated that compounds 7, 11, 21, 24 and 26 (*A. baumannii*), as well as compound 9 (*P. aeruginosa*), can alter the biofilm structure (Table 3). With respect to the HTS broad spectrum agents, only compound 3 demonstrated killing of established *P. aeruginosa* biofilm. These same four compounds, however, caused changing of the pre-existing *S. epidermidis* biofilm structure. Further among this group, compounds 7, 8 and 11 caused dispersion of established *P. aeruginosa* biofilm at 300 μM, as demonstrated by reduced biofilm thickness (FIG. 1B). Compounds 18, 24, 26, and 31 were effective at selectively inhibiting and/or killing only *A. baumannii* biofilms and demonstrated killing of established biofilm culture (FIG. 3B and FIG. 5). However, with the exception of compound 3, the HTS hit compounds that effectively inhibited and/or killed *P. aeruginosa* and *A. baumannii* biofilms or only *P. aeruginosa* biofilms were unable to kill either of these established bacterial biofilms.

Figure 6B:
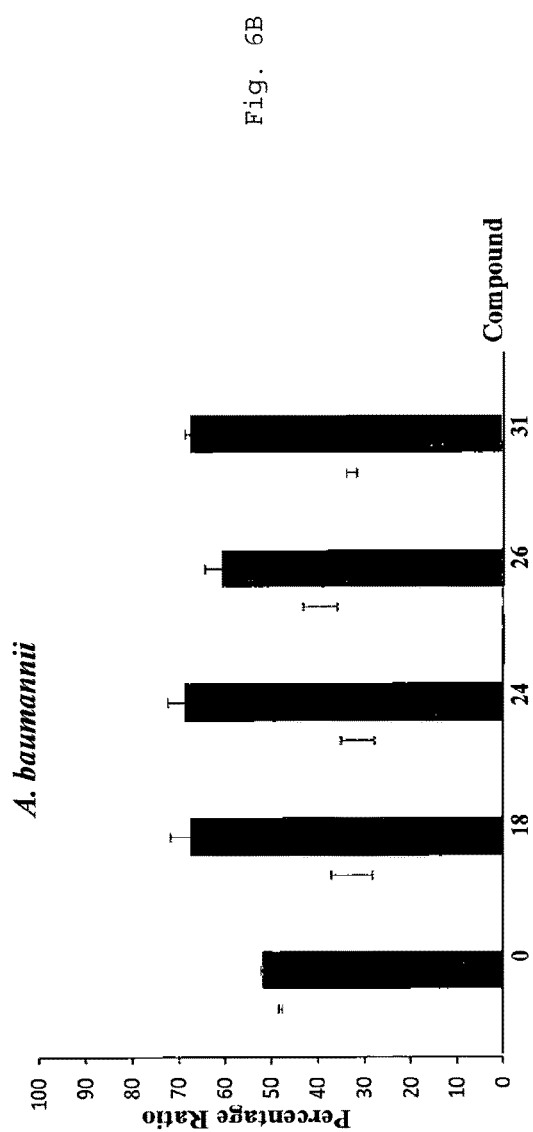

The confirmed HTS hit compounds were also subject to cytotoxicity testing. The broad spectrum agents demonstrated lower cytotoxicity in the two human cell types used in this study, differentiated THP-1 and A549 (FIG. 6). MIC assays were also performed for the broad spectrum agents. All four showed MIC values lower than 20 μM for *A. baumannii*. Compounds 7 and 8, both quinolones, had lower MIC values under both aerobic and anaerobic conditions against *S. epidermidis* and *P. aeruginosa*. Compound 11, which is also a quinolone showed a lower MIC for *S. epidermidis*, but not *P. aeruginosa*. Interestingly, compound 3, an isothiazolone, showed higher MIC in all conditions and bacteria used in this study (Table 2).

Several clear classes of compounds emerge within these hits. The dominant class comprises of a number of quinolone analogs. This class includes compounds 7 and 9, which are close analogs/pro-drugs of ciprofloxacin, whose mode of action is known to be dependent upon inhibition of DNA gyrase. Typical of quinolone structure-activity relationships, the greatest antibacterial potency was seen with the presence of a charged nitrogen in the 7 position substituent as in compound 11, Table 2. The observation of quinolone related compounds showing strong antibacterial and antibiofilm activity underscores the validity of the screening process in identifying antibiotic compound actives from a very large library. Among this group, compounds 7, 8 and 11 are effective at inhibiting biofilm development and/or killing established biofilms with respect to all three microorganisms, while compounds 9 and 14 were only effective against *P. aeruginosa*.

The second most prominent class is that of the phenolic hydrazones. Structurally, the phenol-hydrazone portion shows very high similarity across the series, with an m-hydroxyl and/or o- and p-halogenations; both factors enhancing redox properties of the molecules. Conversely, a wide range of variance at the other end of the structures seems well tolerated. Compound 29 also shares the halo phenol motif, although it lacks the hydrazone functions, and may or may not be mechanistically related. This series consistently shows inhibition of biofilm formation activity against *A. baumannii*; yet lacks significant growth inhibitory activity. This activity profile appears also to be unique to the *Acinetobacter* species.

Remaining compound classes included benzimidazole, furazan, catechol, sulfonamide, dioxime, pyrazole, acylpyruvate and isothiazolone. Benzimidazoles are known to be biofilm inhibitors. Moreover, 2-aminoimidazoles are known both for biofilm inhibiting activity and efficacy for dispersing biofilms. The two benzimidazoles compounds identified include compound 1 and compound 31 which were effective in both gram-negative microbes used in this study or only *A. baumannii*, respectively. Compound 1 did not show efficacy for dispersion in either of *A. baumannii* and *P. aeruginosa* biofilms (FIG. 2B). On the other hand, compound 31 did demonstrate dispersion activity in *A. baumannii* biofilm (FIG. 3B). Moreover, compound 31 also demonstrated ability in killing established *A. baumannii* biofilm.

The following examples illustrate several specific embodiments and aspects of the invention and are not intended to limit the full scope of the invention as defined by the claims appended hereto.

Example 1

This Example illustrates application of an embodiment of the HTS for identifying agents from a library of compounds effective for inhibiting biofilm formation and/or killing an established biofilm.

A subset of 42,865 compounds representing a diverse cross section of a large University Compound Library were used in a high through-put screen according to the invention to identify compounds that inhibited *P. aeruginosa*, and/or *A. baumannii* biofilm formation and/or killed established biofilms form from these bacterial species.

Each HTS tier consisted of: (i) primary screening, (ii) confirmation screening and (iii) dose-response curve screening. Each tier of HTS included three distinct biological process assays. The first assay was an optical density measurement of bacteria growth in the presence of each compound reported as a total bacteria growth. In the second assay, resazurin solution was used as an indicator of metabolic activity to measure the live bacteria in the biofilms, reported as live biofilm. The final assay was crystal violet staining, which indicated the amount of biofilm formation and the effect of each compound on this process, reported as total biofilm formation. A compound was identified as an HTS hit compound if it exhibited an $AC_{50} \leq 20$ µM in at least one biological assay (total bacteria growth, total biofilm formation or live biofilm) from the dose response screen.

Briefly, stationary phase bacteria grown in L-broth were diluted 1:200 into fresh L-broth and 50 µM of each test compound. After 20-24 hours, the optical density ($OD_{560}$) of each suspension was measured using Zeiss Plate::Vision with a 560 BP filter (560 nm, 2.5% light intensity, 1 mm focus to bottom of plate, and exposure time of 100 ms). To measure bacterial viability in the biofilm, 50 µl of a 5 mg/ml resazurin solution in L-broth was added to each well after washing 3 times with 50 µl of PBS. The plates were then incubated at 37° C. for 30 or 180 min for *A. baumannii* and *P. aeruginosa* biofilms, respectively. Fluorescence was measured using Zeiss Plate::Vision at excitation and emission wavelengths of 535 and 580 nm, 100 ms exposure time, 2.5% intensity and a 2 mm focus to the bottom of the biofilms. To assess biofilm formation, plates were washed 3 times with PBS and then 50 µl of 0.01% of crystal violet was added to each well to assess bacterial biofilm formation as described in a similar borosilicate tube assay by O'Toole and Kolter. After incubation at room temperature for 30 min and removal of the crystal violet solution by washing with PBS, 95% ethanol was added to solubilize the crystal violet followed by incubation for 20 min at room temperature. Finally, the optical density of each plate was determined using measured by Zeiss Plate::Vision using the same settings used to measure total bacterial growth. These 3 steps were used in each of the three tiers for the HTS process: (i) single point primary screening at 10 µM, (ii) triplicate confirmation of hits from (i) at 10 µM and (iii) determination of $AC_{50}$ values in 10 point dose-response at a concentration range of 0.1-50 µM) in hits from (ii). The $AC_{50}$ represents the concentration of compound that inhibits 50% of bacterial growth, bacterial viability, or biofilm formation. Genedata Screener® Assay Analyzer Software (Ver. 9.0.0 Standard) was used to analyze data from all assay tiers. Compounds with an $AC_{50}$ of less than 20 µM in one of the biological assays from the dose response screen were subject to additional investigation.

Results.

HTS hit compounds were classified as single, dual or broad spectrum agents depending on how many of the bacterial species the compound was effective against. Results showed seven compounds that were effective against both *P. aeruginosa* and *A. baumannii*, (1 isothiazolone, 3 quinolones, 1 benzimidazole, 1 furazan, and 1 catechol), three effective against *P. aeruginosa* alone (2 quinolones and 1 aryl heterocycle), and thirteen effective only against *A. baumannii* (1 sulfonamide, 1 dioxime, 4 halophenols, 2 catechols, 1 pyrrole, 1 quinolone, 1 benzimidazone, 1 acylpyruvate, and 1 benzimidazole), respectively. Of the seven dual agent hits, four compounds were found to be efficacious in all three bacteria (1 isothiazolone and 3 quinolones). A summary of the hits, including, compound class, and values for the $AC_{50}$, is set forth in Table 1 and the chemical structures are provided in Table 2. In addition, the compound names are provided in Table 5.

With respect to the single agent compounds effective only for inhibiting and/or killing of *A. baumannii* biofilm formation, the majority of this group (21, 23, 25 and 33) are halophenols. In contrast, compound 24 is catechol, while compounds 29 and 30 are benzimidazoles. The remaining compounds, 17, 18, 26, and 30 represent sulfonamide, dioxime, pyrazoles, quinolone and acylpyruvate, respectively. Among this group, compounds 17 and 18 were effective at inhibiting in all assays of the HTS on *A. baumannii* biofilms. Compounds 21, 23-26, 30 and 33 were effective against biofilm formation (total biofilm formation) and also against established biofilm (live biofilm), while compound 29 and 33 were only effective on biofilm formation or killing of the biofilm, respectively (see Table 1).

The single agent compounds effective for inhibiting formation and/or killing only *P. aeruginosa* biofilm are designated compounds 9 and 14. The results from the HTS assay showed that compound 9 is effective at reducing total biofilm formation and live biofilm cells in *P. aeruginosa* and compound 14 affected bacterial growth and total biofilm formation (Table 1).

The dual agent compounds effective for inhibiting formation and/or killing of *A. baumannii* and *P. aeruginosa* biofilms include compounds 1, 2 and 12, which are a benzimidazole, a furazan and a catechol, respectively (see Table 1). Moreover, these compounds also had a negative impact on total bacterial growth with the exception of compound 12 on *P. aeruginosa* (Table 1).

The broad spectrum compounds include compounds 3, 7, 8, and 11. These compounds possessed the ability to inhibit and/or kill *P. aeruginosa*, *S. epidermidis* and *A. baumannii* biofilms (Table 1). Compounds 7, 8 and 11 are of the quinolone class, and compound 3 is an isothiazolone. The HTS results indicate that compounds 3, 7 and 11 were very effective during all phases of the screening process; (i) total bacteria growth, (ii) bacterial viability and (iii) total biofilm formation, predictably showing a low $AC_{50}$ value. In contrast, compound 8 was more effective at inhibiting *S. epidermidis* than *P. aeruginosa* or *A. baumannii* and it showed a higher $AC_{50}$ in the HTS assay, except for the total biofilm formation of *P. aeruginosa* ($AC_{50}$ of 10.34 μM) (Table 1).

TABLE 1

Summary of AC50 of hit compounds for each microorganism and at individual step assay

| | | | Dose Response | | |
|---|---|---|---|---|---|
| Compound | Class | Bacteria | Total Bacteria Growth $AC_{50}$ (uM) | Total Biofilm Formation $AC_{50}$ (uM) | Live Biofilm $AC_{50}$ (uM) |
| 3 | Isothiazolone | *A. baumannii* | 2.93 | 4.45 | 4.04 |
| | | *P. aeruginosa* | 9.27 | 3.07 | 13.37 |
| | | *S. epidermidis* | 8.89 | 8.84 | 8.61 |
| 7 | Quinolones | *A. baumannii* | 12.10 | 17.67 | 8.45 |
| | | *P. aeruginosa* | 3.00 | 7.81 | 0.38 |
| | | *S. epidermidis* | 2.20 | 1.12 | 0.85 |
| 8 | Quinolones | *A. baumannii* | 3.44 | 4.18 | 2.33 |
| | | *P. aeruginosa* | 44.39 | 10.34 | 57.00 |
| | | *S. epidermidis* | <0.1 | <0.1 | <0.1 |
| 11 | Quinolones | *A. baumannii* | 0.66 | 0.85 | 0.61 |
| | | *P. aeruginosa* | 16.00 | 7.40 | 9.60 |
| | | *S. epidermidis* | <0.1 | <0.1 | <0.1 |
| 1 | Benzimidazoles | *A. baumannii* | <0.3 | <0.3 | <0.3 |
| | | *P. aeruginosa* | <0.3 | <0.3 | <0.3 |
| 2 | Furazan | *A. baumannii* | 2.21 | 3.15 | 3.21 |
| | | *P. aeruginosa* | 9.09 | 1.43 | 15.19 |
| 12 | Catechol | *A. baumannii* | 4.43 | 7.17 | 6.10 |
| | | *P. aeruginosa* | 35.62 | 13.45 | 19.06 |
| 9 | Quinolones | *P. aeruginosa* | 27.70 | 3.60 | 8.14 |
| 14 | Quinolones | *P. aeruginosa* | 13.64 | 12.95 | 80.09 |
| 17 | Sulfonamide | *A. baumannii* | 0.96 | 0.88 | 0.45 |
| 18 | Dioximes | *A. baumannii* | 17.71 | 14.56 | 4.53 |
| 21 | Halophenol | *A. baumannii* | NS* | 14.58 | 9.86 |
| 23 | Halophenol | *A. baumannii* | >200 | 17.52 | 8.97 |
| 24 | Catechol | *A. baumannii* | >200 | 3.75 | 1.13 |
| 25 | Halophenol | *A. baumannii* | >200 | 5.11 | 1.26 |
| 26 | Pyrazoles | *A. baumannii* | NS* | 7.60 | 8.07 |
| 29 | Halophenol | *A. baumannii* | NS* | 8.37 | >200 |
| 30 | Acylpyruvate | *A. baumannii* | NS* | 8.54 | 2.35 |
| 31 | Benzimidazoles | *A. baumannii* | >200 | 23.54 | 17.45 |
| 33 | Halophenol | *A. baumannii* | >200 | 17.22 | 7.28 |

*No sigmoid curve has been observed in the dose response assay.

TABLE 2

Structures of compounds demonstrating efficacy as summarized in Table 1

| ID | Structure |
|---|---|
| 7 | [Structure of compound 7: fluoroquinolone with piperazine-thiocarbamoyl substituent and cyclopropyl N-group] |
| 8 | [Structure of compound 8: fluoroquinolone with hydroxyazetidine substituent, cyclopropyl N-group, and additional fluorine] |
| 9 | [Structure of compound 9: naphthyridine carboxylic acid with piperazine-dithiocarbamate substituent and tert-butyl N-group] |
| 11 | [Structure of compound 11: fluoroquinolone with pyridine substituent, cyclopropyl N-group, and additional fluorine] |

TABLE 2-continued

Structures of compounds demonstrating efficacy as summarized in Table 1

| ID | Structure |
|---|---|
| 14 | 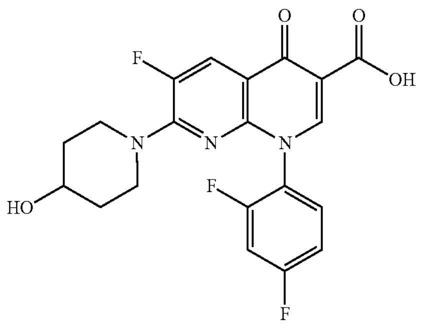 [SMILES: O=C(O)c1cn(-c2ccc(F)cc2F)c2nc(N3CCC(O)CC3)c(F)cc2c1=O] |
| 2 | 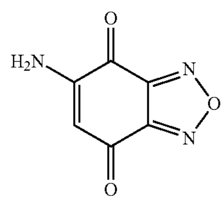 |
| 3 | 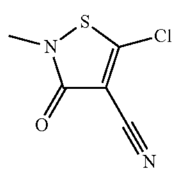 |
| 1 | 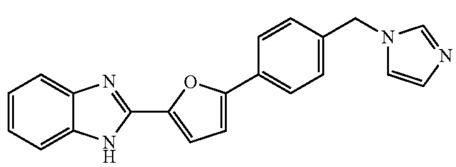 [SMILES: c1ccc2[nH]c(-c3ccc(-c4ccc(Cn5ccnc5)cc4)o3)nc2c1] |
| 30 | 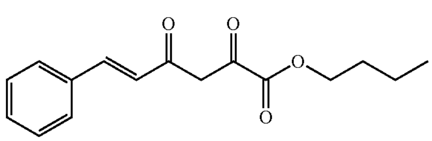 [SMILES: CCCCOC(=O)C(=O)CC(=O)/C=C/c1ccccc1] |
| 26 | 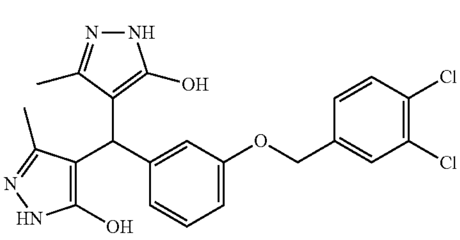 [SMILES: Cc1n[nH]c(O)c1C(c1cccc(OCc2ccc(Cl)c(Cl)c2)c1)c1c(C)n[nH]c1O] |
| 12 | 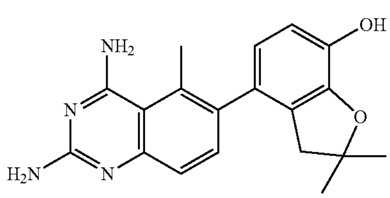 [SMILES: Cc1c(-c2ccc(O)c3c2CC(C)(C)O3)ccc2nc(N)nc(N)c12] |
| 17 | |
| 18 | |
| 21 | |
| 23 | |
| 25 | |
| 33 | |

TABLE 2-continued

Structures of compounds demonstrating efficacy as summarized in Table 1

| ID | Structure |
|---|---|
| 31 | 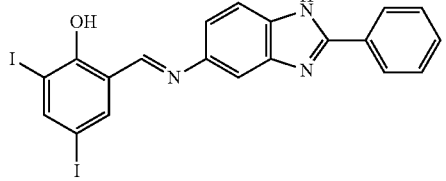 |
| 29 | 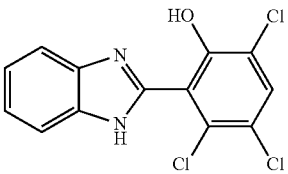 [SMILES: Oc1c(Cl)cc(Cl)c(Cl)c1-c1nc2ccccc2[nH]1] |
| 24 | 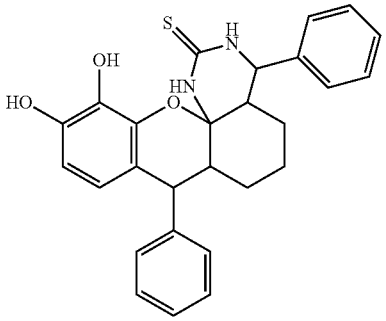 [SMILES: Oc1ccc2c(c1O)OC13NC(=S)NC(c4ccccc4)C1CCCC3C2c1ccccc1] |

Example 2

This Example illustrates confirmation of the HTS hit compounds by Confocal Laser Scanning Microscopy (CLSM).

Broad spectrum agents (effective against all three bacterial species) and single agent compounds identified as HTS hits were investigated with CLSM confirmation of inhibition of biofilm formation (culture of bacteria with compounds) or killing of bacteria residing within an established biofilm (compound addition after culturing biofilm). To evaluate inhibition of *P. aeruginosa* biofilms, bacteria were sub-cultured into 10% L-broth and grown at 37° C. until the $OD_{600}$ reached 0.25. The bacteria were further diluted 1:100 into a modified 0.5×M63 minimum media (50 mM $KH_2PO_4$, 7.5 mM $(NH_4)_2SO_4$, 9 μM $FeSO_4$, 0.5% casamino acids, 0.2% glucose, and 1 mM $MgSO_4$). *A. baumannii* biofilms were also grown in 10% L-broth until the $OD_{600}$ reached 0.05 but diluted 1:10 into 5% L-broth media. *S. epidermidis* biofilm cultures were grown. Briefly, the bacteria were grown in TSB until the $OD_{600}$ reached 0.75, and a 1:100 dilution of the bacteria was sub-cultured into phosphate buffered saline (PBS). All of the biofilm bacterial cultures were grown in 96-well plate chambers (MatTek Corp., Ashland, Mass.) in the presence of 10 μM of each compound or DMSO as a control and incubated for 18 hrs at 37° C. To investigate the ability of compounds to kill bacteria within pre-existing biofilms, biofilms were grown under the same conditions, but without test compound. These biofilms were washed once with PBS and incubated an additional 24 hr at 37° C. in PBS containing 300 μM of each compound. All biofilm cultures were then washed twice with 100 μL of PBS and stained using the LIVE/DEAD® BacLight™ Bacterial Viability Kit (Invitrogen). Finally, biofilm images were obtained using a Zeiss LSM510 META Confocal Microscope (Carl Zeiss, Inc., Germany). A 488 nm laser was used in conjunction with a Plan-Apochromat 100×/1.4 Oil DIC objective. Z-stacks were 8 bit and measured 127.3 μm×127.3 μm×16.0 μm in size. The filters used were 505-530 and 620-680 IR, as the excitation and emission wavelengths for red fluorescence are 490 nm and 635 nm, respectively, and 480 nm and 500 nm for green fluorescence. Three dimensional images were generated using the "Projection" ability on LSM Image Browser software (v.1.4.0.121) or Zeiss LSM image browser software version 3.5 (Carl Zeiss, Inc., Germany), and Live/Dead calculations were conducted based upon these images using MacBiophotonics ImageJ following the guidelines in the cell counting guide by C. Labno {Rasband, 1997-2011 #25; Labno, #2} at the University of Chicago Integrated Light Microscopy Core. The thickness of the biofilm was calculated using Comstat software. A hit was defined as a >50% dead to live ratio.

The CLSM experiment was performed in one or two or all bacteria used in this study depending on its activity. For the validation of HTS hits, 10 μM of compound was added to each bacterial suspension and the resulting biofilm stained with LIVE/DEAD® BacLight™ Bacterial Viability Kit. The images were analyzed to determine the live and dead ratios of biofilm bacteria, the thickness of biofilms, and structural attributes of biofilms.

Results

A summary of results is set forth in Table 3. The CLSM results showed that three of the four broad agent compounds; compounds 3, 7, and 8, were effective at inhibiting *P. aeruginosa*, *A. baumannii*, and *S. epidermidis* biofilms formation (FIG. 1A, A-D and K-N, both top and sagittal views), and, with the exception of compound 8 in *P. aeruginosa*, each compound killed residential bacteria present in the established cultures (red, the propidium iodide fluorescence). Compound 11, a quinolone, had no effect on inhibiting *P. aeruginosa* biofilm formation. However, this compound altered the biofilm structure and inhibited biofilm formation of *A. baumannii*. Compound 11 also inhibited and killed *S. epidermidis* biofilm cultures (FIG. 1A, E, O and J, both top and sagittal views, respectively).

For the dual agent (*P. aeruginosa* and *A. baumannii*) group, CLSM results confirmed that compounds 1, 2, and 12, a benimidazole, furazan, and catechol respectively, were all capable of inhibiting biofilm formation in both organisms and, with the exception of compound 12 in *P. aeruginosa*, effectively killed the residential bacteria (FIGS. 2A and 2B). The *P. aeruginosa* single agent compound 14, a quinolone, inhibited biofilm formation and was also lethal to residential bacteria (FIG. 4). Finally, of the *A. baumannii* single agent compounds, CLSM validated seven of the thirteen HTS hits. Two compounds were effective at biofilm inhibition (compounds 17 and 18, a sulfonamide and a dioxime, respectively); four compounds were effective in killing the bacterium (compounds 17, 18, 31, and 34, a sulfonamide, dioxime, benzimidazole, and catehol respectively); and three compounds (compounds 21, 24, and 26, a halophenol, a catechol, and a pyrazole respectively) affected biofilm structure (FIGS. 3A and 3B).

The broad agent compounds, CLSM assay and live and dead calculation of the broad spectrum compound group revealed that compound 3 (an isothiazolone) was effective at killing bacteria biofilm resident of *P. aeruginosa* at 300 μM and at 100 μM. This compound was also determined to alter the structure of *S. epidermidis* biofilms. Compounds 7, 8, and 11 (three quinolones) altered the morphology of *P. aeruginosa* but exhibited minimal effects otherwise (FIG. 1B). Compound 7 was also effective at 100 μM. Treatment with compounds 8 and 11 at 300 μM on established *P. aeruginosa* biofilms led to thinner biofilm architecture. None of the dual agent (*P. aeruginosa* and *A. baumannii*) HTS hits compounds were confirmed effective in killing established biofilms (FIG. 2A and FIG. 2B). One difference was that compound 9 failed to inhibit biofilm formation but did cause the bacteria to form loosely packed biofilms compared to control biofilm culture (FIGS. 5C, A and B). Even though this compound at 300 μM failed to kill bacteria within a biofilm, it did cause the dispersion of the established biofilms after treatment for 24 hr, similar to what was observed with respect to compound 9 (FIG. 5D).

*A. baumannii* single agent CLSM results showed that compounds 18, 24, 26, 28, 31, 34 (dioxime, catechol, pyrazoles, quinolone, benzimidazole, and catechol, respectively) were effective against biofilm resident *A. baumannii*, while compounds 21, 24, and 26 (halophenol, catechol, and pyrazoles, respectively) appeared to alter the structure of the biofilm (FIGS. 3A and 3B).

The broad spectrum agent compounds 3, 7, 8, and 11 were confirmed to possess the ability to inhibit and/or kill *P. aeruginosa*, *S. epidermidis* and *A. baumannii* biofilms, respectively (Table 1). Compounds 7, 8 and 11 are of the quinolone class, except compound 3, which is an isothiazolone. The HTS assay results indicated that compounds 3, 7 and 11 were very effective in all screening processes (i) total bacteria growth, (ii) bacterial viability and (iii) total biofilm formation, predictably yielding a low $AC_{50}$ value. In contrast, compound 8 was more effective at inhibiting *S. epidermidis* than *P. aeruginosa* or *A. baumannii* and compound 8 showed a higher $AC_{50}$ in the HTS assay for all results except for total biofilm formation of *P. aeruginosa* ($AC_{50}$ of 10.34 μM) (Table 1).

TABLE 3

Summary of Results From Confocal Laser Scanning Microscopy

| | | HTS assay results | | | CLSM Results | | | | | |
|---|---|---|---|---|---|---|---|---|---|---|
| | | | | | Co-culture of bacteria with compound | | | Effect of compound on the pre-existing biofilm | | |
| C | Bacteria | Total Bacteria growth | Live Bacteria | Biofilm Formation | Inhibit biofilm formation | Killing | Biofilm structural changed | Killing | Dispersion | Biofilm structural changed |
| 3 | *A. baumannii* | Y | Y | Y | Y | Y | — | — | — | — |
| | *P. aeruginosa* | Y | Y | Y | Y | Y | — | Y | — | — |
| | *S. epidermidis* | Y | Y | Y | Y | Y | — | — | — | Y |
| 7 | *A. baumannii* | Y | Y | Y | Y | Y | Y | — | — | — |
| | *P. aeruginosa* | Y | Y | Y | Y | Y | — | — | Y** | — |
| | *S. epidermidis* | Y | Y | Y | Y | Y | — | — | — | — |
| 8 | *A. baumannii* | —* | —* | —* | Y | Y | — | — | — | — |
| | *P. aeruginosa* | —* | Y | —* | Y | — | — | — | Y** | — |
| | *S. epidermidis* | Y | Y | Y | Y | Y | — | — | — | — |
| 11 | *A. baumannii* | Y | Y | Y | — | — | Y | — | — | — |
| | *P. aeruginosa* | Y | Y | Y | — | — | — | — | Y** | — |
| | *S. epidermidis* | Y | Y | Y | Y | Y | — | — | — | — |
| 1 | *A. baumannii* | Y | Y | Y | Y | Y | — | — | — | — |
| | *P. aeruginosa* | Y | Y | Y | Y | Y | — | — | — | — |
| 2 | *A. baumannii* | Y | Y | Y | Y | Y | — | — | — | — |
| | *P. aeruginosa* | Y | Y | Y | Y | Y | — | — | — | — |
| 12 | *A. baumannii* | Y | Y | Y | Y | Y | — | — | — | — |
| | *P. aeruginosa* | — | Y | Y | Y | — | — | — | — | — |
| 9 | *P. aeruginosa* | — | Y | Y | — | — | Y | — | Y | — |
| 14 | *P. aeruginosa* | Y | Y | — | Y | Y | — | — | Y | — |
| 17 | *A. baumannii* | Y | Y | Y | Y | Y | — | — | — | — |
| 18 | *A. baumannii* | Y | Y | Y | Y | Y | — | Y | — | — |
| 21 | *A. baumannii* | — | Y | Y | — | — | Y | — | — | Y |
| 23 | *A. baumannii* | — | Y | Y | — | — | — | — | — | — |
| 24 | *A. baumannii* | — | Y | Y | — | — | Y | Y | — | Y |
| 25 | *A. baumannii* | — | Y | Y | — | — | — | — | — | — |
| 26 | *A. baumannii* | — | Y | Y | — | — | Y | Y | — | Y |
| 29 | *A. baumannii* | — | Y | — | — | — | — | — | — | — |
| 30 | *A. baumannii* | — | Y | Y | — | — | — | — | — | — |
| 31 | *A. baumannii* | — | — | Y | — | Y | — | Y | — | — |
| 33 | *A. baumannii* | — | Y | Y | — | — | — | — | — | — |

*AC50 higher than 20 μM
**Bacterial morphology changed

Example 3

This Example illustrates a cytotoxicity assay of compounds identified as HTS broad-agent hits.

Following identification as an HTS broad spectrum hit and confirmation by CLSM, a cytotoxicity assay was performed on compounds 3, 7, 8 and 11. The lactate dehydrogenase assay (LDH) is commonly used as an enzymatic marker to quantitatively correlate cell death via leakage of the enzyme from dead or dying cells. An LDH assay was used to investigate the toxicity of compounds on A549 and differentiated THP-1 cells. Cells were grown as described previously then cells were washed once with 200 μl of fresh, pre-warmed media before the experiment was performed by the addition of 100 μl of media alone, media with DMSO, or media with compound (ranging from 10-300 μM) and the cells were then incubated for 48 hrs under the same conditions. After 48 hr incubation of cells with each compound, LDH assays were performed using the CytoTox-One Homogenous Membrane Integrity Assay Kit (Promega). The plates were incubated at room temperature for 30 min before the addition of 20 µl of 1% Triton-X-100 into the positive control wells with DMSO treated cell lines for 15 min. The supernatant and CytoTox-One reagent were then added together (1:1) in a new 96 well plate. After shaking for 30 seconds, the new plate was incubated at room temperature for 10 min. Finally, 25 µl of Stop Solution was added, incubated at room temperature for 5 min, and the fluorescence signal was detected using a Synergy 2 Multi-Mode Microplate Reader (Ex. 560 nM/Em. 590). The unit of measurement is the Relative Fluorescence Unit (RFU). The cytotoxicity of the compounds was calculated based on the percentage of compound RFUs measured (Experimental) in comparison to the RFU of the DMSO treated cells as those that were completely lysed (Maximum LDH Release). The equation used for calculation of cytotoxicity is given below:

$$\text{Percent cytotoxicity} = 100 \times \frac{(\text{Experimental} - \text{Culture Medium Background})}{(\text{Maximum } LDH \text{ Release} - \text{Culture Medium Background})}$$

Results

The cytotoxicity of the broad agent hit compounds was examined in differentiated human THP-1, a human acute monocytic leukemia cell line and A549, a human lung adenocarcinoma epithelial cell line. Since all compounds from the library were solubilized in DMSO, it was first necessary to determine the potential toxicity of DMSO alone on these cell lines. We examined the effect of DMSO concentrations from 3-6%, was assessed on these THP-1 and A549 cells and. determined DMSO had a minimal effect, as 6% DMSO was only 30-40% cytotoxic toward both A549 and differentiated THP-1 cells. Compounds were assessed at varying concentrations of 0, 260, 290, 300, and 570 µM for compounds 7, 11, 8, and 3, respectively, for the cytotoxicity assays. The calculation of the cytotoxicity of compounds was compared with the DMSO treated cell control. The results showed none of the compounds were found to be very significantly toxic (those that killed >50%) to differentiated THP-1 or A549 cells at the highest concentrations used in this study (FIG. 3), with the exception of compound 3 at 57 µM that show 60% of cytotoxicity on the differentiated THP-1 cell. However, for unknown reasons, this cytotoxity was decreased at a 10-fold higher concentration, 570 µM (FIG. 3A).

Example 4

This Example illustrates determination of a Minimal Inhibitory Concentration (MIC) and MIC Determination of Gram negative and Gram positive Broad Spectrum Agent HTS hits compounds.

A standard protocol for determining the MIC of a specific compound as outlined by the Clinical and Laboratory Standards Institute (CLSI) was used, based on growth of the selected bacteria in Mueller Hinton (MH) broth with subsequent 2-fold dilutions of compounds of interest. Following the CLSI protocols, the MIC of each broad spectrum "hit" compound was performed in all 3 bacterial species in both aerobic and anaerobic conditions. All bacteria were grown in MH broth for 18 hrs at 37° C. The cells were then diluted 100-fold into MH broth containing compounds at concentrations ranging from 0.40-50 µM in the presence of either $KNO_3$ or glucose to allow bacterial growth under anaerobic condition. After 24 hrs of incubation, cell growth was measured at $OD_{600}$ using a SpectraMax 190 Absorbance Microplate Reader.

The HTS and CLSM assays identified and confirmed compounds that can inhibit biofilms formation in aerobic growth conditions. However, P. aeruginosa and S. epidermidis are capable of growth under anaerobic as well as aerobic conditions. Anaerobic conditions have been shown to exist in mature biofilms as regions near the substrate become oxygen depleted with growth of the film. The Minimal Inhibitory Concentrations (MIC) of the four broad agent hit compounds under both aerobic and anaerobic conditions of planktonic P. aeruginosa and S. epidermidis cultures were determined to evaluate compound efficacy in different growth conditions. The MICs for A. baumannii were determined only in aerobic conditions. To examine growth in aerobic conditions, bacteria were grown in either Mueller Hinton (MH) media only, MH media in the presence of 1% $KNO_3$, or MH in the presence of 1% glucose. For MIC determinations under anaerobic conditions, growth was examined in MH media with 1% $KNO_3$ or with 1% glucose. The MIC results for all three organisms are shown in Table 4.

TABLE 4

The Minimum Inhibition Concentration for Planktonic of A. Baumanii, P. Aeruginosa and S. Epidermidis planktonic cell cultures under different growth conditions.

| | P. aeruginosa | | | S. epidermidis | | | | | A. baumanii |
|---|---|---|---|---|---|---|---|---|---|
| | MH | MH with 1/% $KNO_3$ | | MH | MH with 1% $KNO_3$ | | MH with 1% Glucose | | MH |
| | Aerobic | Aerobic | Anaerobic | Aerobic | Aerobic | Anaerobic | Aerobic | Anaerobic | Aerobic |
| 3 | >50* | 33.33 ± 8.33 | 25 ± 0 | 20.83 ± 4.17 | 25 ± 0 | 16.67 ± 4.17 | 10.42 ± 2.08 | 16.67 ± 4.17 | 6.25 ± 2.21 |
| 7 | 4.7 ± 1.04 | 5.21 ± 1.04 | 4.17 ± 1.04 | 8.33 ± 2.08 | 10.42 ± 2.08 | 5.21 ± 1.04 | 5.86 ± 2.42 | 5.21 ± 1.04 | 16.67 ± 4.17 |
| 8 | 10.42 ± 2.08 | 20.83 ± 4.17 | 7.81 ± 2.71 | 0.65 ± 10.13 | 0.78 ± 0.39 | 0.39 ± 0 | 0.65 ± 0.13 | 0.78 ± 0.39 | 1.37 ± 0.64 |
| 11 | >50 | >50 | 25 ± 12.5 | 5.73 ± 3.42 | 7.81 ± 2.71 | 4.17 ± 1.04 | 7.81 ± 2.71 | 7.29 ± 2.76 | 5.12 ± 1.04 |

For P. aeruginosa planktonic cultures, compound 7 was the most effective in all growth conditions, requiring only 4-5 µM to inhibit planktonic P. aeruginosa growth. Compound 8 was less effective, requiring 7 µM under anaerobic conditions and up to 20 µM for aerobic conditions in the presence of $KNO_3$. Compounds 3 and 11 were much less effective against P. aeruginosa, requiring 25 µM and higher for anaerobic and aerobic conditions respectively. S. epidermidis planktonic cultures were most sensitive to compound 8 where less than 1 µM was necessary to inhibit growth under all conditions. Compounds 7 and 11 were also effective in anaerobic as well as aerobic conditions, requiring from 4-10 µM depending on the media and condition used. Compound 3 was the least effective in *S. epidermidis* cultures, requiring 10-25 µM. *A. baumannii* planktonic cultures were most susceptible to compound 8 which required roughly 1 µM to inhibit growth. Compounds 3 and 11 had similar MICs from 5-6 µM and compound 7 was the least effective at 16 µM. In summary, the broad agent compounds were effective against planktonic *P. aeruginosa*, *S. epidermidis* and *A. baumannii* in aerobic and anaerobic conditions at low micromolar concentrations.

Example 5

This Example illustrates efficacy of compounds Se-1 through Se-16 at inhibiting *S. epidermidis* biofilm formation and/or killing established *S. epidermidis* biofilms. Detailed methods, materials and data are set forth in Shea, Chloe, U of Cincinnati Masters Thesis "Effectiveness of Novel Compounds at Inhibiting and Killing *P. aeruginosa* and *S. epidermidis* Biofilms" published on Mar. 17, 2013, the entire disclosure of which is incorporated herein by this reference. FIG. 8 illustrates effective inhibition of Se biofilm formation. For these experiments, Se was co-cultured with 10 µM of compounds Se-1 through Se-16 (see Table 5 for compound names and Table 6 for compound structures). A-H represents the top view of the Se biofilm, while the sagittal view is shown in I-P. The control Se biofilm is shown in A/I. Se biofilm formation in the presence of 10 µM of compound Se-3, Se-4, Se-13, Se-14, Se-15 or Se-16 as shown in B/J, C/K, D/L, E/M, F/N, G/O, and H/P, respectively. FIG. 9 illustrates effective killing of established Se biofilm. For this experiment, Se biofilms were treated with 300 µM of compounds Se-1 through Se-16. A-H represents the top view of the Se biofilm, while the sagittal view is shown in I-P. The control Se biofilm is shown in A/I. Effective killing was defined as >50% dead bacteria. The results are summarized in Table 7.

TABLE 5

| | HTS hits Compound Names |
|---|---|
| 3) | 5-chloro-2-methyl-3-oxo-1,2-thiazole-4-carbonitrile |
| 7) | 7-(4-carbamothioylpiperazin-1-yl)-1-cyclopropyl-6-fluoro-4-oxoquinoline-3-carboxylic acid |
| 8) | 1-cyclopropyl-6,8-difluoro-7-(3-hydroxyazetidin-1-yl)-4-oxoquinoline-3-carboxylic acid |
| 11) | 7-(4-pyridyl)-1-cyclopropyl-6,8-difluoro-4-oxoquinoline-3-carboxylic acid 1 2-[5-[4-(4,5-dihydroimidazol-1-ylmethyl)phenyl]-2-furanyl]-1H-Benzimidazole |
| 2) | 5-amino-2,1,3-Benzoxadiazole-4,7-dione |
| 12) | 6-(2,3-dihydro-2,2-dimethyl-4-benzofuranyl)-5-methyl-2,4-Quinazolinediamine |
| 9) | 1-(1,1-dimethylethyl)-1,4-dihydro-6-fluoro-4-oxo-7-(4-dithiocarboxypiperazin-1-yl)-1,8-Naphthyridinyl-3-carboxylic acid |
| 10) | N-(4-chlorophenyl)-5-(trifluoromethyl)-1,3,4-thiadiazol-2-amine |
| 14) | 1-(2,4-difluorophenyl)-6-fluoro-1,4-dihydro-4-oxo-7-(4-hydroxy-1-piperidinyl)-1,8-Naphthyridine-3-carboxylic acid |
| 17) | 3-phenoxy-N-[4-(trifluoromethyl)phenyl]-Benzenesulfonamide |
| 18) | N-(4-nitroso-2-phenyl-1H-indol-5-yl)hydroxylamine |
| 21) | 2-[2-[(4-amino-1,2,5-oxadiazol-3-yl)-1H-benzimidazol-1-yl]-N'-[(E)-(3,5-dibromo-2-hydroxyphenyl)methylidene]acetohydrazide |
| 23) | N'-[(E)-(5-Bromo-2,4-dihydroxyphenyl)methylene]naphtho[2,1-b]furan-2-carbohydrazide |
| 24) | (4R,4aR,7aS,8S,13aR)-rel-3,4,4a,5,6,7,7a,8-octahydro-11,12-dihydroxy-4,8-diphenyl-[1]Benzopyrano[3,2-i]quinazoline-2(1H)-thione |
| 25) | N'1,N'3-Bis [(E)-(5-bromo-2-hydroxyphenyl)methylene]-2-butylmalonohydrazide |
| 26) | 4-[{3-[(3,4-dichlorobenzyl)oxy]phenyl}(5-hydroxy-3-methyl-1H-pyrazol-4-yl)methyl]-3-methyl-1H-pyrazol-5-ol |
| 28) | N-2-(4-methoxybenzothiazolyl)-2,3-dihydro-4-Methyl-5-oxo-1H,5HBenzo[ij]quinolizine-6-carboxamide |
| 29) | 2-(1H-benzoimidazol-2-YL)-3,4,6 Trichlrophenol |
| 30) | Butyl (E)-2,4-dioxo-6-phenylhex-5-enoate |
| 31) | Benzimidazol-5-yl)imino]methyl}phenol |
| 33) | N'-(2,4-dihydroxybenzylidene)-2-phenylquinoline-4-carbohydrazide |
| 34) | 3,4,5',6'-tetrahydro-6',6'-dimethyl-4-phenyl-2'-(2-propen-1-ylthio)-spiro[2H-1-benzopyran-2,4'(3'H)-pyrimidine]-7,8-diol |
| Se-1) | N-(3-cyano-5,6-dihydro-4H-cyclopenta[d]thiophen-2-yl)-2-[(4 methylphenyl)sulfonylamino]benzamide |
| Se-2) | N-(4-chloro-3-morpholin-4-ylsulfonylphenyl)-2-[(5-chlorothiophen-2-yl)sulfonylamino]benzamide |
| Se-3) | 4-{[4-(dimethylamino)phenyl]methyl}-N-[4-(trifluoromethyl)phenyl]piperazine-1-carboxamide |
| Se-4) | 2-dodecoxyethyl-bis(2-hydroxyethyl)-(phenylmethyl)ammonium |
| Se-5) | N'-[(1E)-(3-bromo-4-hydroxyphenyl)methylidene]-1,5-diphenyl-1H-1,2,4-triazole-3-carbohydrazide |
| Se-6) | 3-(4-methoxyphenyl)-5-phenyl-2-(trifluoromethyl)-4H,7H-pyrazolo[1,5-a]pyrimidin-7-one |
| Se-7) | 2-[(5-bromothiophen-2-yl)sulfonylamino]-N-(phenylmethyl)benzamide |
| Se-8) | N-[2-(4-chlorophenyl)ethyl]-4-piperidin-1-ylsulfonyl-1H-pyrrole-2-carboxamide |
| Se-9) | 7-[(3S)-3-(aminomethyl)pyrrolidin-1-yl]-1-cyclopropyl-6-fluoro-8-methoxy-4-oxo-1,4-dihydroquinoline-3-carboxylic acid |
| Se-10) | 1-(4-chlorophenyl)-3-[5-(trifluoromethyl)-1,3,4-thiadiazol-2-yl]urea |
| Se-11) | 3-[3-(4-bromo-1-methyl-1H-pyrazol-3-yl)phenyl]-1-[4-(trifluoromethoxy)phenyl]urea |
| Se-12) | (2E)-3-keto-3-(2-thienyl)-2-[[4-(trifluoromethoxy)phenyl]hydrazono]propionitrile |

TABLE 5-continued

HTS hits Compound Names

Se-13) [4-[bis(4-dimethylaminophenyl]methylene]-1-cyclohexa-2,5-dienylidene]-dimethyl-ammonium
Se-14) 2-(4-ethyl-3,5-dimethyl-1H-pyrrol-2-yl]acetic acid
Se-15) 2-[(4-bromophenyl)sulfonylamino]-N-(3-fluorophenyl)benzamide
Se-16) 5,7-dibromo-2-methylquinolin-8-ol

TABLE 6

| No. | Structure | Class |
| --- | --- | --- |
| Se1 | 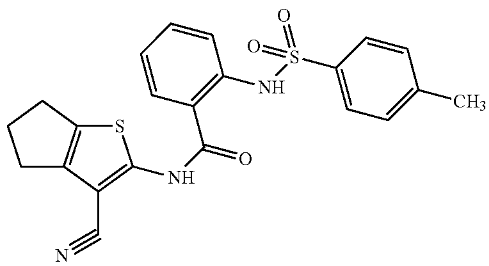 [SMILES: Cc1ccc(S(=O)(=O)Nc2ccccc2C(=O)Nc2sc3c(c2C#N)CCC3)cc1] | Diaryl-sulfonamide |
| Se2 | 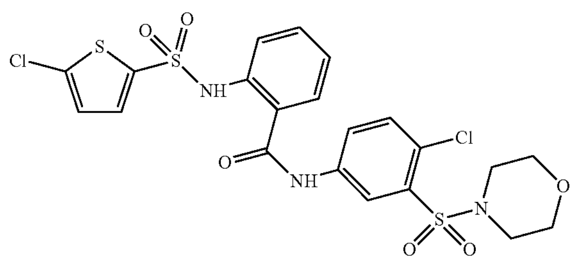 [SMILES: O=C(Nc1ccc(Cl)c(S(=O)(=O)N2CCOCC2)c1)c1ccccc1NS(=O)(=O)c1ccc(Cl)s1] | Diaryl-sulfonamide |
| Se3 | 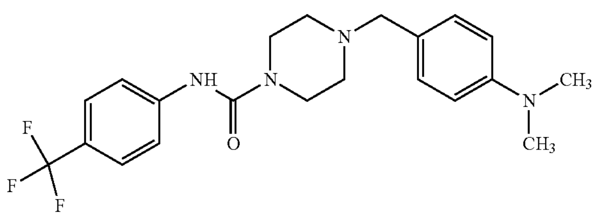 [SMILES: CN(C)c1ccc(CN2CCN(C(=O)Nc3ccc(C(F)(F)F)cc3)CC2)cc1] | Urea |
| Se4 | 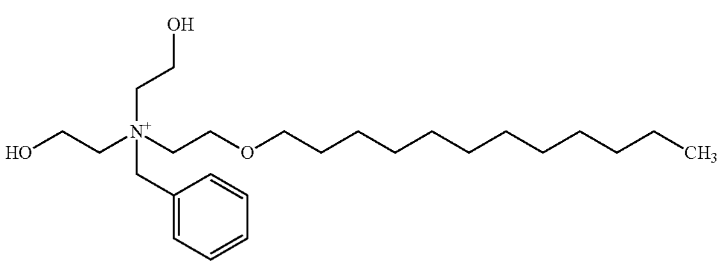 [SMILES: CCCCCCCCCCCCOCC[N+](CCO)(CCO)Cc1ccccc1] | Quaternary Ammonium Salt |
| Se5 | 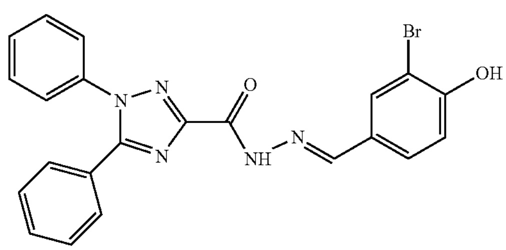 [SMILES: O=C(N/N=C/c1ccc(O)c(Br)c1)c1nc(-c2ccccc2)n(-c2ccccc2)n1] | Hydrazone |

TABLE 6-continued
| No. | Structure | Class |
|---|---|---|
| Se6 | 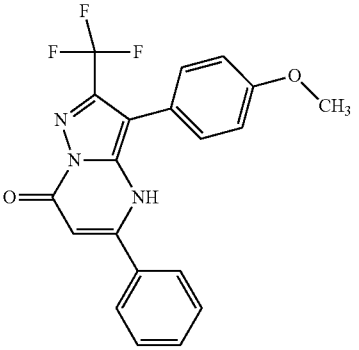 [SMILES: COc1ccc(-c2c(C(F)(F)F)nn3c(=O)cc(-c4ccccc4)[nH]c23)cc1] | Pyrazolo-pyrimidine |
| Se7 | 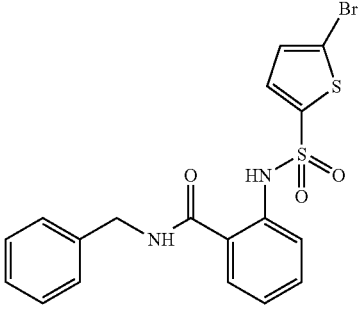 [SMILES: O=C(NCc1ccccc1)c1ccccc1NS(=O)(=O)c1ccc(Br)s1] | Diaryl-sulfonamide |
| Se8 | 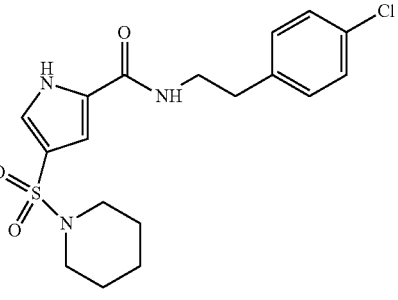 | Sulfonamide |
| Se9 | 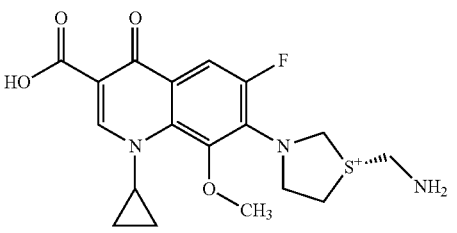 [SMILES: COc1c(N2CC[S@@+](CN)C2)c(F)cc2c(=O)c(C(=O)O)cn(C3CC3)c12] | Quinolone |
| Se10 | 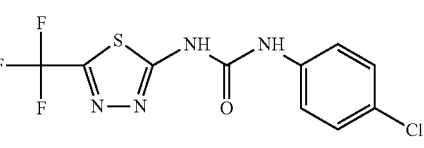 | Urea |

TABLE 6-continued

| No. | Structure | Class |
|---|---|---|
| Se11 | 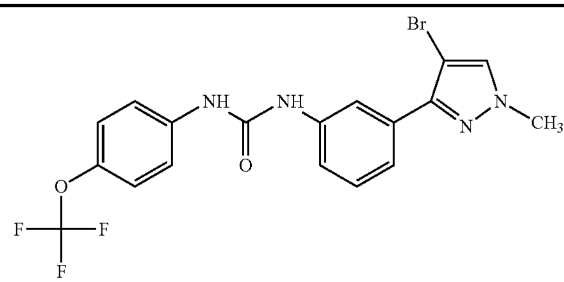 | Urea |
| Se12 | 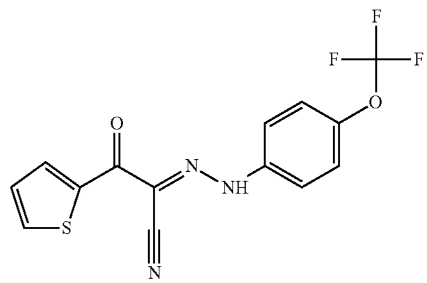 [SMILES: N#C/C(=N\Nc1ccc(OC(F)(F)F)cc1)C(=O)c1cccs1] | Hydrazone |
| Se13 | 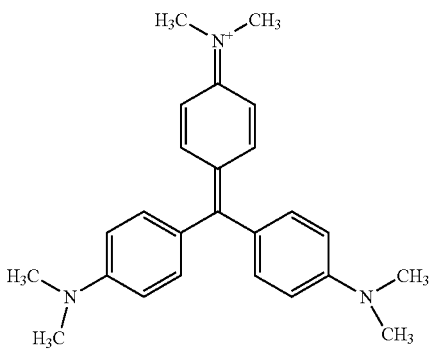 | Dye |
| Se14 | 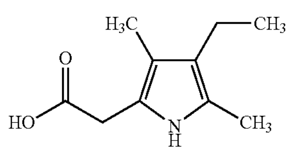 | Pyrrole |
| Se15 | 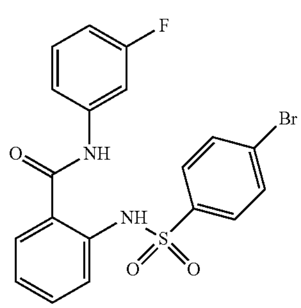 [SMILES: O=C(Nc1cccc(F)c1)c1ccccc1NS(=O)(=O)c1ccc(Br)cc1] | Diaryl-sulfonamide |
| Se16 | 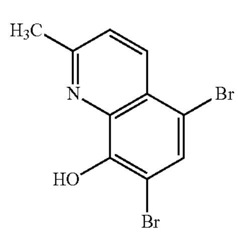 | 8-Hydroxy-quinoline |

TABLE 7

| Compound | Inhibition | Killing | Dispersion | Morphology Change |
|---|---|---|---|---|
| Se1 | O | O | O | O |
| Se2 | O | O | O | O |
| Se3 | X | X | O | O |
| Se4 | X | X | O | O |
| Se5 | O | O | O | O |
| Se6 | O | O | O | O |
| Se7 | O | O | O | O |
| Se8 | O | O | O | O |
| Se9 | X | O | O | O |
| Se10 | O | X | O | O |
| Se11 | O | O | O | O |
| Se12 | O | X | O | O |
| Se13 | X | X | O | O |
| Se14 | X | X | O | O |
| Se15 | X | X | O | O |
| Se16 | X | O | O | O |

What is claimed is:

1. A compound effective for inhibiting bacterial biofilm formation and/or killing established bacterial biofilm, wherein the bacteria is one or more of *S. epidermidis*, *P. aeruginosa*, and *A. baumannii*, and the compound is selected from the compounds set forth in Table 1.

2. The compound according to claim 1 effective for killing established *A. baumannii* biofilm, wherein the compound is selected from compounds 1, 2, 12, 17, 18, and 31, having respective chemical structures

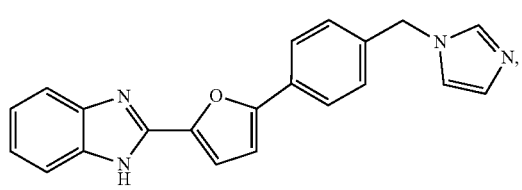

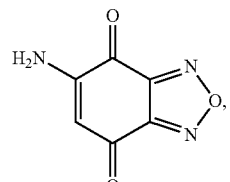

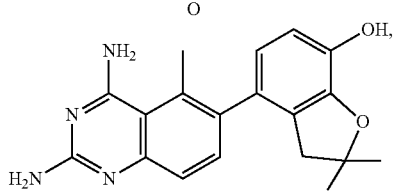

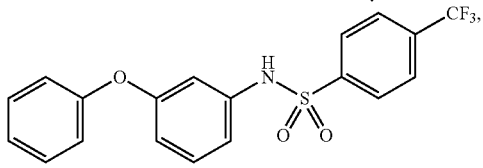

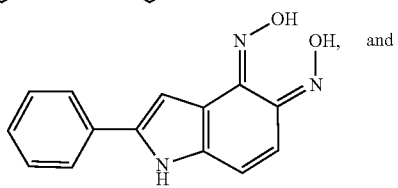

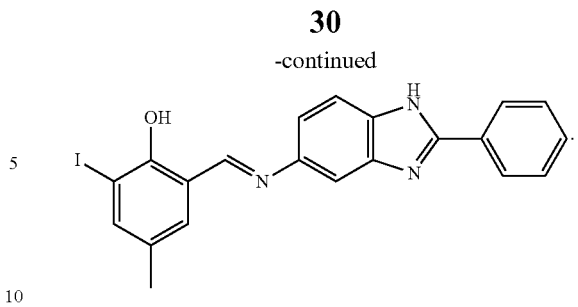

3. The compound according to claim 1 effective for inhibiting formation of an *A. baumannii* biofilm, wherein the compound is selected from compounds 1, 2, 12, 17, and 18, having respective chemical structures

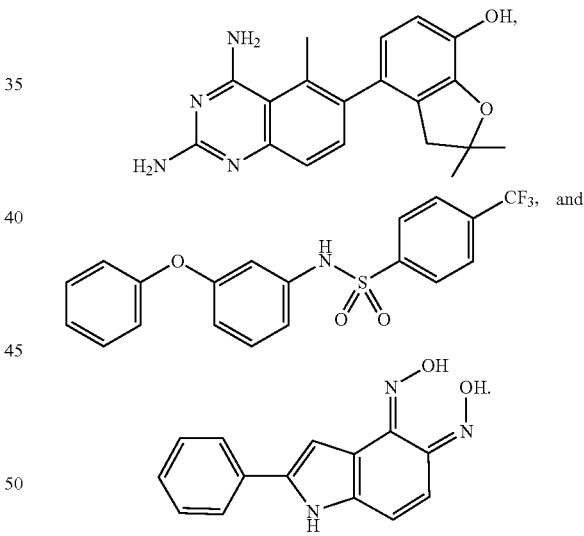

4. The compound according to claim 1 effective for inhibiting formation of a *P. aeruginosa* biofilm, wherein the compound is selected from compounds 1, 2, 12, and 14, having respective chemical structures

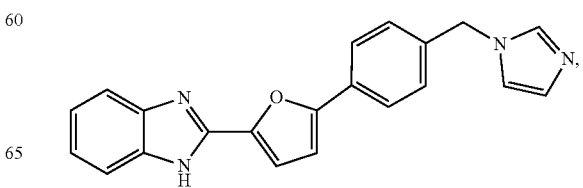

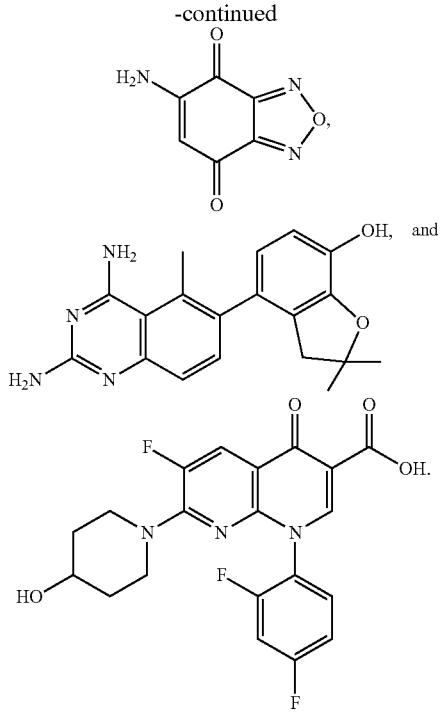

5. The compound according to claim 4, further effective for killing established *P. aeruginosa* biofilm, wherein the compound is selected from compounds 1, 2, and 14, having respective chemical structures

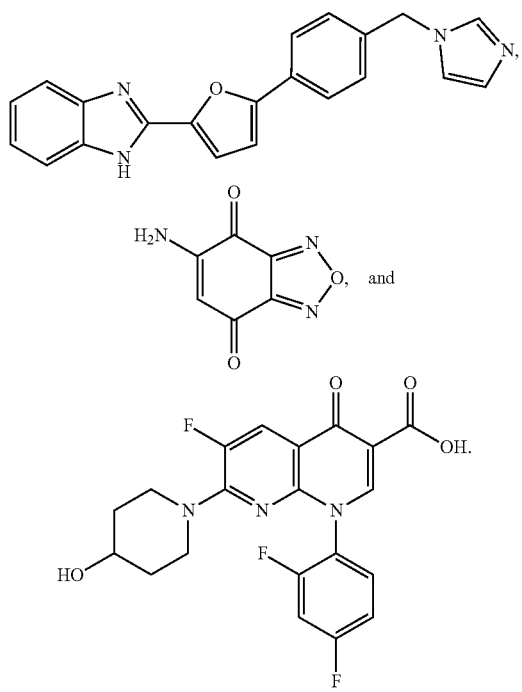

6. The compound according to claim 1 effective for inhibiting formation of both a *P. aeruginosa* biofilm and an *A. baumannii* biofilm, wherein the compound is selected from compounds 1, 2, and 12, having respective chemical structures

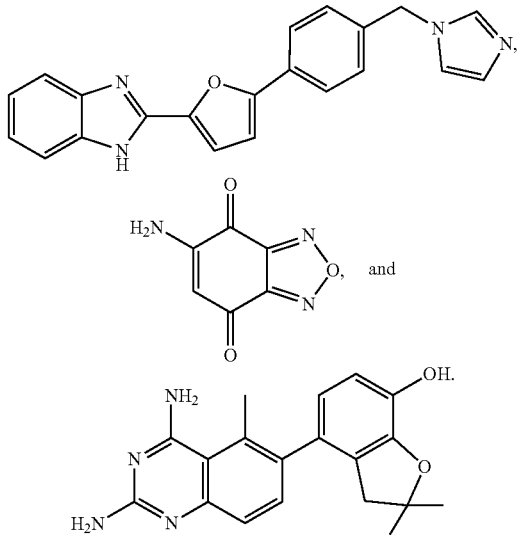

7. The compound according to claim 6, further effective as a bactericide against *P. aeruginosa* and *A. baumannii*, wherein the compound is selected from compounds 1 and 2, having respective chemical structures

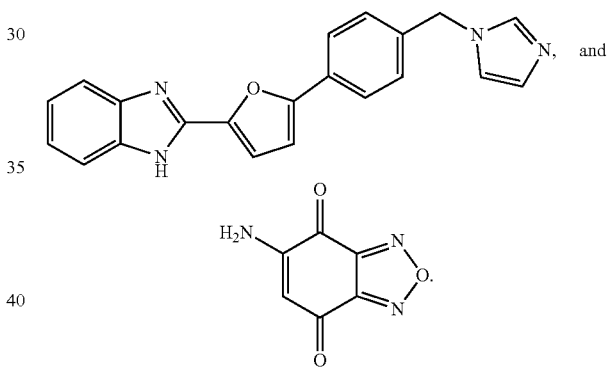

8. The compound according to claim 1, effective for inhibiting formation of any one of an *S. epidermidis* biofilm, a *P. aeruginosa* biofilm, and an *A. baumannii* biofilm, wherein the compound is selected from compounds 3, 7, and 8, having respective chemical structures

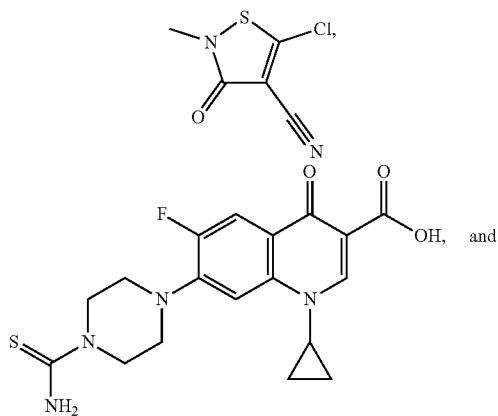

-continued

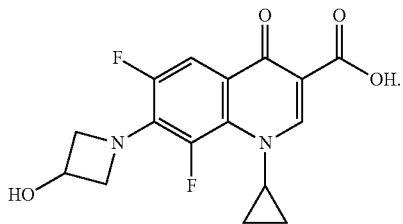 [SMILES: O=C(O)c1cn(C2CC2)c2c(F)c(N3CC(O)C3)c(F)cc2c1=O]

9. The compound according to claim 8, further effective for killing any one of an established *S. epidermidis* biofilm, an established *P. aeruginosa* biofilm, and an established *A. baumannii* biofilm, wherein the compound is selected from compounds 3 and 7, having respective chemical structures

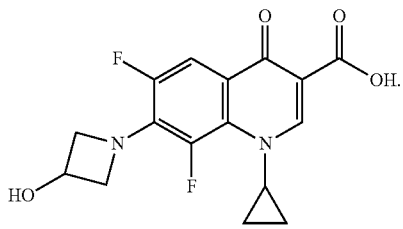

10. The compound according to claim 8, further effective for killing any one of an established *S. epidermidis* biofilm and an established *A. baumannii* biofilm, wherein the compound is compound 8, having chemical structure

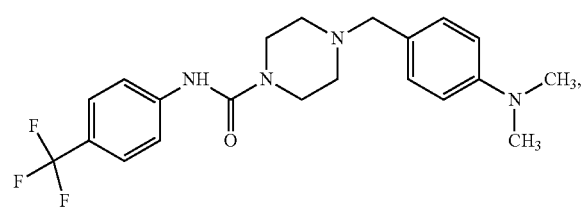

11. A compound effective for inhibiting formation of an *S. epidermidis* biofilm, wherein the compound is selected from compounds Se-3, Se-4, Se-9, Se-14, Se-15, and Se-16, having respective chemical structures -continued

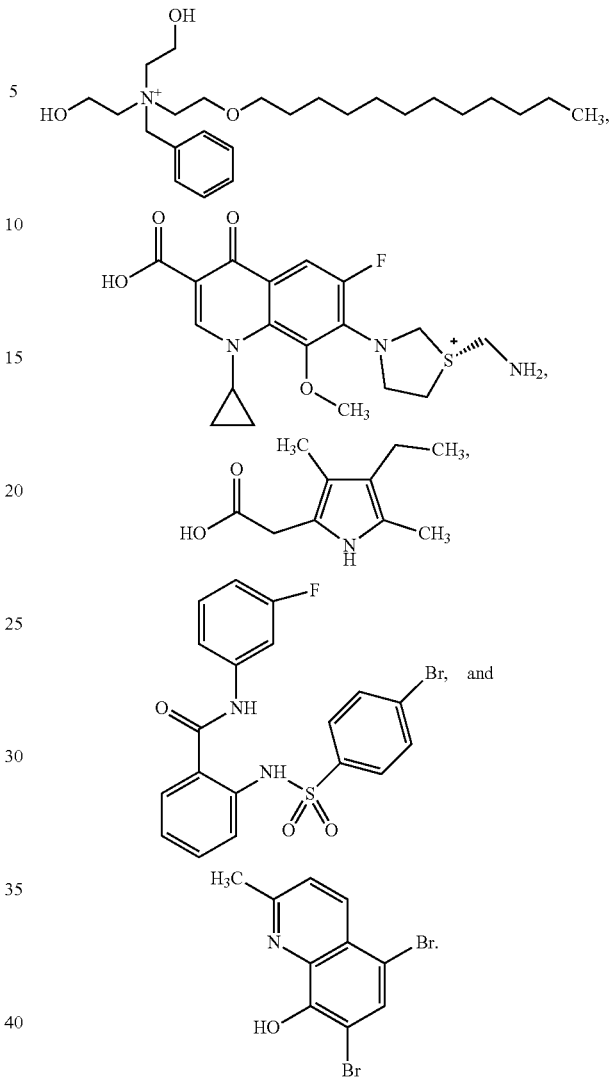

12. The compound according to claim 11, further effective for killing an *S. epidermidis* biofilm, wherein the compound is selected from compounds Se-3, Se-4, and Se-15, having respective chemical structures

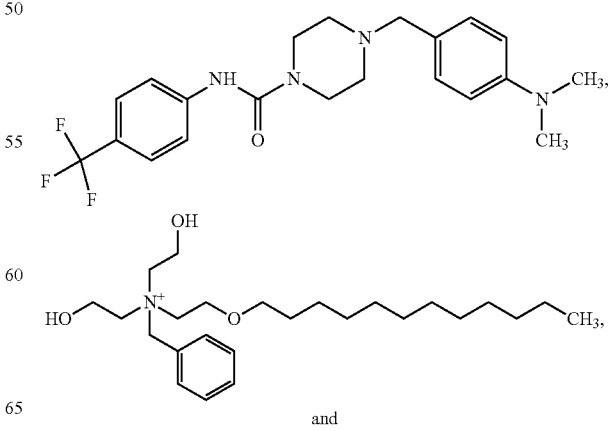

and

-continued
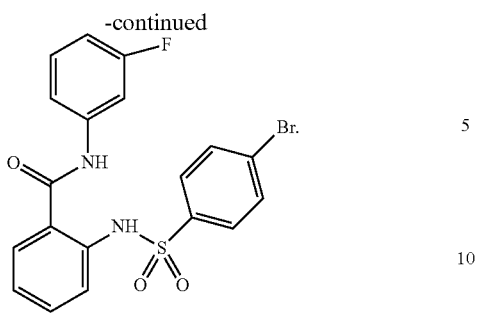
5
10
13. A compound effective for inhibiting bacterial biofilm formation and/or killing established bacterial biofilm, wherein the bacteria is one or more of *S. epidermidis, P. aeruginosa,* and *A. baumannii,* and the compound is compound 34, having compound name 3,4,5',6'-tetrahydro-6',6'-dimethyl-4-phenyl-2'-(2-propen-1-ylthio)-spiro[2H-1-benzopyran-2,4'(3'H)-pyrimidine]-7,8-diol.
* * * * *